(12) United States Patent
Alvarez et al.

(10) Patent No.: US 12,347,546 B2
(45) Date of Patent: Jul. 1, 2025

(54) VIRTUAL ARTICULATION MODEL FOR DENTAL TREATMENT

(71) Applicant: Solventum Intellectual Properties Company, Maplewood, MN (US)

(72) Inventors: Alberto Alvarez, Madrid (ES); Richard E. Raby, Lino Lakes, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 800 days.

(21) Appl. No.: 17/626,152

(22) PCT Filed: Jul. 17, 2020

(86) PCT No.: PCT/IB2020/056756
§ 371 (c)(1),
(2) Date: Jan. 11, 2022

(87) PCT Pub. No.: WO2021/009724
PCT Pub. Date: Jan. 21, 2021

(65) Prior Publication Data
US 2022/0246270 A1 Aug. 4, 2022

Related U.S. Application Data

(60) Provisional application No. 62/875,854, filed on Jul. 18, 2019.

(51) Int. Cl.
*G16H 20/40* (2018.01)
*A61C 7/00* (2006.01)
(Continued)

(52) U.S. Cl.
CPC ............. *G16H 20/40* (2018.01); *A61C 11/00* (2013.01); *A61C 13/34* (2013.01); *A61C 7/002* (2013.01);
(Continued)

(58) Field of Classification Search
CPC ........... A61C 9/0004; A61C 9/05; A61C 9/06; A61C 9/07
See application file for complete search history.

(56) References Cited

U.S. PATENT DOCUMENTS

2002/0177108 A1* 11/2002 Pavlovskaia ............. A61C 5/77
433/213
2006/0263739 A1* 11/2006 Sporbert ............... A61C 9/0053
433/213

(Continued)

FOREIGN PATENT DOCUMENTS

CN 107301673 10/2017
WO WO 2014-060595 4/2014
(Continued)

OTHER PUBLICATIONS

International Search Report for PCT International Application No. PCT/IB2020/056756, mailed on Oct. 12, 2020, 3 pages.
(Continued)

*Primary Examiner* — Wen W Huang

(57) ABSTRACT

The invention relates to a method for determining whether a tooth is correctly shaped and oriented to avoid interference with another tooth using virtual articulation. The method comprises a) receiving data indicative of a virtual dentition of an oral cavity of a patient by a computing device, the data indicative of the virtual dentition including data indicative of at least one of a virtual mandibular arch representing a mandibular arch of the patient or a virtual maxillary arch representing a maxillary arch of the patient; b) receiving data indicating a selected point on the virtual dentition of the oral cavity; and c) determining a tangent vector indicating a direction of motion of the selected point and determining whether the orientation of a tooth of the virtual dentition or the shape of the tooth is correctly shaped and oriented based
(Continued)

on the determined tangent vector, wherein the tangent vector is based on a rotational axis of the virtual mandibular arch.

20 Claims, 19 Drawing Sheets

(51) Int. Cl.
    *A61C 11/00*     (2006.01)
    *A61C 13/34*     (2006.01)
    *G06T 7/73*     (2017.01)

(52) U.S. Cl.
    CPC ...... *G06T 7/74* (2017.01); *G06T 2207/30036* (2013.01)

(56) References Cited

U.S. PATENT DOCUMENTS

| | | | | |
|---|---|---|---|---|
| 2007/0099146 | A1* | 5/2007 | Reising | A61C 3/00 433/24 |
| 2010/0138025 | A1* | 6/2010 | Morton | G06F 17/10 700/103 |
| 2013/0006659 | A1 | 3/2013 | Fisker et al. | |
| 2013/0066598 | A1* | 3/2013 | Fisker | A61C 19/05 703/1 |
| 2015/0005798 | A1 | 2/2015 | See et al. | |
| 2015/0057983 | A1* | 2/2015 | See | G16B 5/00 703/1 |
| 2015/0379780 | A1* | 12/2015 | Jin | A61B 6/463 345/419 |
| 2018/0000537 | A1 | 1/2018 | Alvarez et al. | |
| 2018/0005377 | A1* | 1/2018 | Alvarez | G06T 7/74 |
| 2019/0076214 | A1* | 3/2019 | Nyukhtikov | A61C 7/002 |
| 2021/0192759 | A1* | 6/2021 | Lang | A61B 90/98 |
| 2023/0069649 | A1* | 3/2023 | Goldston | G06F 16/41 |
| 2023/0320824 | A1* | 10/2023 | Roschin | G16H 30/40 433/214 |

FOREIGN PATENT DOCUMENTS

| | | |
|---|---|---|
| WO | WO 2018-005071 | 1/2018 |
| WO | WO 2018-211361 | 11/2018 |
| WO | WO 2019-009992 | 1/2019 |

OTHER PUBLICATIONS

Extended European Search Report, EP20841105.8, dated Jul. 3, 2023, 4 pages.

\* cited by examiner

VIRTUAL ARTICULATION MODEL FOR DENTAL TREATMENT

CROSS REFERENCE TO RELATED APPLICATIONS

This application is a national stage filing under 35 U.S.C. 371 of PCT/IB2020/056756, filed 17 Jul. 2020, which claims the benefit of U.S. Provisional Application No. 62/875,854, filed 18 Jul. 2019, the disclosures of which are incorporated by reference in their entireties herein.

TECHNICAL FIELD

This disclosure relates to dental treatment planning using virtual articulation.

BACKGROUND

Digital dentistry is a growing trend with an increasing number of dentists using digital impressioning systems. These systems use an intra-oral scanning camera, or scanning of a traditional physical impression, and an associated processing system to generate a digital three-dimensional (3D) model of patients' teeth (e.g., a patient's maxillary and mandibular arches). The digital 3D models can then be used to make physical models for prosthodontic or orthodontic treatment planning.

An orthodontist or dentist may utilize physical models of the patient's teeth to determine how to re-orient and/or re-shape the patient's teeth to enable the teeth to fit together when the patient's mouth is closed. Typically, physical models are cast in dental stone from physical impressions. Simple bite registration is accomplished using a wax bite plate or full-bodied impression material that captures upper and lower occlusal surfaces simultaneously to relate one arch to the other in space. Dental articulation is accomplished by further capturing the relationship between the bite registration material and points at or near the condyles (such as the ear canals) using a facebow, then transferring this relationship to corresponding stone models of the dental arches mounted in a mechanical articulator. Facebows can fail to accurately capture the true condylar axis due to the ear canals being somewhat displaced from the condyles. They are uncomfortable for the patient, challenging for the clinical practitioner to capture, and require a mechanical instrument to be physically transferred to a dental lab where it is used to register stone castings in a mechanical articulator. This process can take days, or at the very least hours, to complete. The facebow and dental articulator are expensive, and disputes can arise between clinics and labs as to who owns them and when they will be returned to their rightful owners after use. It is also difficult to see and identify contact points on the tooth surfaces when testing the occlusion using such devices, due to the model teeth being completely opaque and obscuring certain contacts from view. Furthermore, it is difficult to measure distances, angles, orientations, areas, and changes over time without the use of a computer operating on 3D digital scan data.

SUMMARY

In general, this disclosure describes techniques for determining whether a tooth is correctly shaped and oriented to avoid interference with another tooth using virtual articulation. Virtual articulation may refer to the measurement and/or visualization of temporomandibular dynamics of a virtual dentition based on three-dimensional scans of a patient's teeth. The virtual dentition may include virtual representations of the patient's mandibular arch and/or maxillary arch. Temporomandibular dynamics may refer to rotation of the virtual dentition about one or more rotational axes. A computing device may utilize a virtual articulation model to determine a tangent vector that indicates motion of a portion of the virtual dentition about one of the rotational axes. The computing device may utilize the tangent vector to determine whether the user's teeth are shaped and/or oriented correctly to reduce or eliminate interference between teeth. Additionally, or alternatively, the techniques of this disclosure may enable a computing device to determine whether roots of the user's teeth are aligned properly for axial loading (e.g., to distribute loads through the teeth and the roots of the teeth to the mandible and maxilla). In another example, the computing device may output a graphical user interface that provides a dental treatment provider with information regarding the shape, orientation, and motion of the teeth during virtual articulation.

The techniques and systems of this disclosure may provide one or more advantages. For instance, the techniques of this disclosure may enable a computing device and/or dental treatment provider to determine the correct position, orientation, and shape of any tooth in a patient's oral cavity based on the patient's own mandibular dynamics, which may reduce or eliminate interference between teeth and thus improve the health and function of the patient's teeth. In another instance, the techniques of this disclosure may enable a computing device and/or dental treatment provider to determine the correct position, orientation, and shape of any tooth in one arch (e.g., the mandibular arch) without information about the dentition of the opposing arch (e.g., the maxillary arch), which may enable the computing device and/or dental provider to more easily reconstruct the dentition (e.g., orthognathic surgery, dentures, dental restorations, among others).

In one example, this disclosure describes a method comprising receiving, by a computing device, data indicative of a virtual dentition of an oral cavity of a patient, the data indicative of the virtual dentition including data indicative of at least one of a virtual mandibular arch representing a mandibular arch of the patient or a virtual maxillary arch representing a maxillary arch of the patient; receiving, by a computing device, data indicating a selected point on the virtual dentition of the oral cavity; determining, by the computing device, based on a rotational axis of the virtual mandibular arch, a tangent vector indicating a direction of motion of the selected point; and performing, by the computing device, an action based on the determined tangent vector.

In another example, this disclosure describes a system comprising a storage device and a processor in communication with the storage device, the processor configured to receive data indicative of a virtual dentition of an oral cavity of a patient, the data indicative of the virtual dentition including data indicative of at least one of a virtual mandibular arch representing a mandibular arch of the patient or a virtual maxillary arch representing a maxillary arch of the patient; receive data indicating a selected point on the virtual dentition of the oral cavity; determine, based on a rotational axis of the virtual mandibular arch, a tangent vector indicating a direction of motion of the selected point; and perform an action based on the determined tangent vector.

In another example, this disclosure describes a non-transitory computer-readable storage medium storing instructions that, when executed, cause at least one processor to receive data indicative of a virtual dentition of an oral cavity of a patient, the data indicative of the virtual dentition including data indicative of at least one of a virtual mandibular arch representing a mandibular arch of the patient or a virtual maxillary arch representing a maxillary arch of the patient; receive data indicating a selected point on the virtual dentition of the oral cavity; determine, based on a rotational axis of the virtual mandibular arch, a tangent vector indicating a direction of motion of the selected point; and perform an action based on the determined tangent vector.

The details of one or more aspects of the disclosure are set forth in the accompanying drawings and the description below. Other features, objects, and advantages will be apparent from the description and drawings, and from the claims.

DETAILED DESCRIPTION

Figure 1:
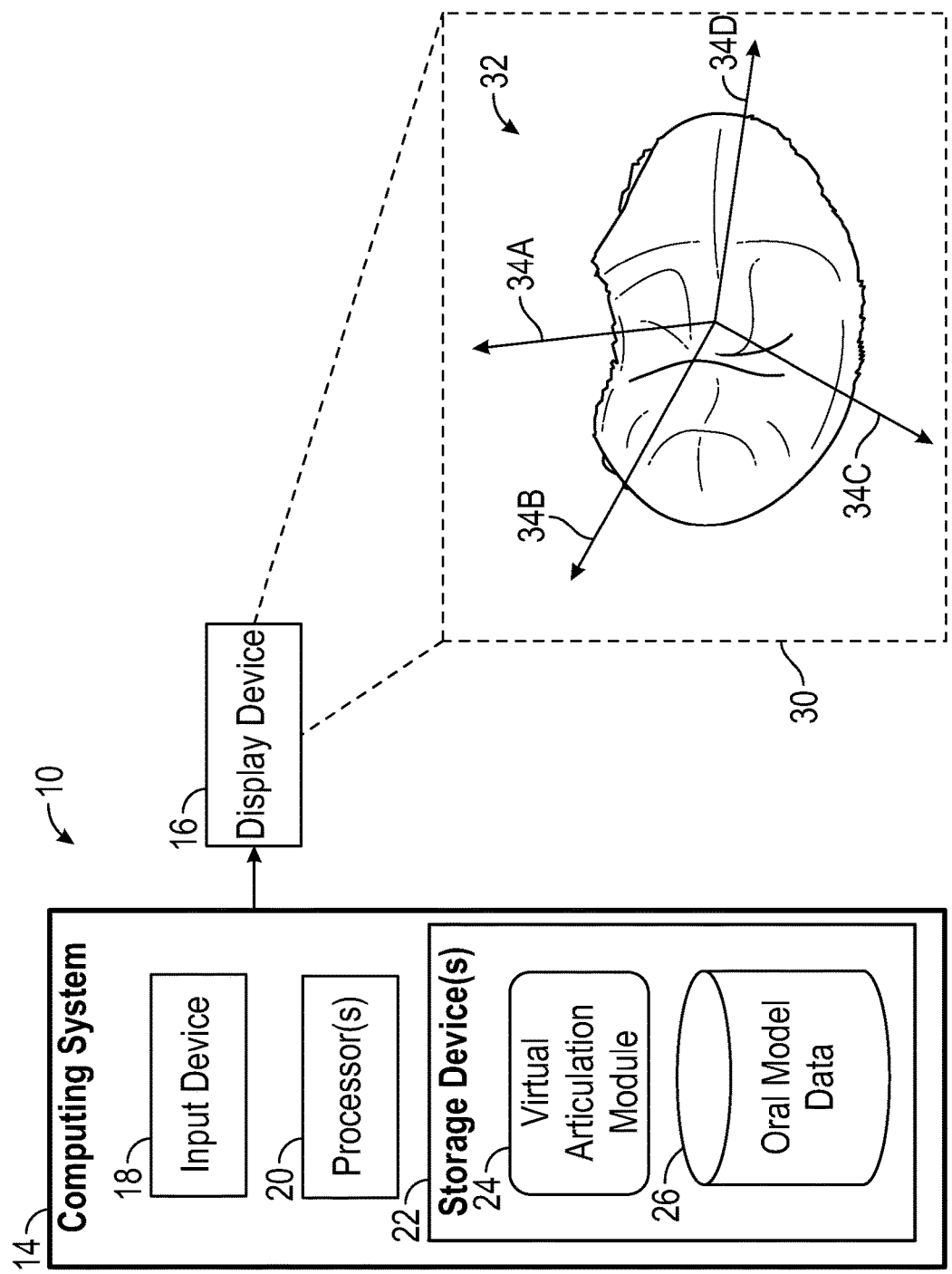
FIG. 1 is a block diagram illustrating an example system for virtual articulation, according to one example of the disclosure.

FIG. 1 is a diagram of an example system 10 for performing virtual articulation and determining whether a patient's tooth is positioned, oriented, or shaped correctly. System 10 includes a computing system 14. Computing system 14 may include a desktop computer, notebook computer, tablet computer, or any type of computing device.

System 10 may also include an electronic display device 16 for displaying digital 3D models of intra-oral structures. In some examples, display device 16 is part of computing system 14, and in other examples, display device 16 may be separate from computing system 14. Display device 16 can be implemented with any electronic display, for example a Cathode Ray Tube (CRT), a liquid crystal display (LCD), light emitting diode (LED) display, or organic light emitting diode (OLED) display.

System 10 may further include an input device 18 for receiving user commands or other information. In some examples, input device 18 is part of computing system 14, and in other examples, input device 18 may be separate from computing system 14. Input device 18 can be implemented with any device for entering information or commands, for example a keyboard, microphone, cursor-control device (e.g., a mouse), or touch screen. The components of system 10 may also be combined, e.g., a tablet computer can incorporate the processor, display and touch screen input devices into a single unit.

Computing system 14 includes one or more processors 20 and one or more storage devices 22. Storage devices 22 may be configured for short-term storage of information as volatile memory and therefore not retain stored contents if deactivated. Examples of volatile memories include random access memories (RAM), dynamic random access memories (DRAM), static random access memories (SRAM), and other forms of volatile memories known in the art. Storage devices 22 may, in some examples, also include one or more computer-readable storage media. Storage devices 22 may be configured to store larger amounts of information than volatile memory. Storage devices 22 may further be configured for long-term storage of information as non-volatile memory space and retain information after activate/off cycles. Examples of non-volatile memories include flash memories, or forms of electrically programmable memories (EPROM) or electrically erasable and programmable (EEPROM) memories.

In various examples, processors 20 may include, be, or be part of programmable processing circuitry, fixed function circuitry, digital signal processors (DSPs), general purpose microprocessors, application specific integrated circuits (ASICs), field programmable gate arrays (FPGAs), or other equivalent integrated or discrete logic circuitry, as well as any combination of such components. In the example of FIG. 1, processor 20 is configured to execute code for virtual articulation module 24 to perform the techniques of this disclosure. The techniques described herein can be implemented in software or firmware modules, for example, for execution by processor 20 or other computing devices. In other examples, the techniques of this disclosure may be implemented in hardware modules or a combination of software and hardware.

In some examples, processors 20 may execute virtual articulation module 24 to determine the correct position, orientation, and shape (also referred to as morphology) of any tooth in the oral cavity based on the patient's own mandibular dynamics, in accordance with the techniques of this disclosure. In another example, virtual articulation module 24 may modify, restore, or create virtual dental anatomy for the patient based on the patient's mandibular dynamics. In this way, virtual articulation module 24 may enable a dental treatment provider (e.g., an orthodontist, dentist, technician, or the like) to create a functional occlusion that is free of interferences and avoids tooth wear, and to reduce or minimize stress on the patient's temporomandibular joint (TMJ) by improving dynamic intercuspation of the teeth. In some examples, creating a functional occlusion free of interferences may also contribute to the long-term stability of the occlusion. Techniques of this disclosure may enable a dental treatment provider to use computing system 14 to diagnose and treat orthodontic malocclusion, bruxing habits, tooth wear, and TMJ disorders. As another example, techniques of this disclosure may enable virtual articulation module 24 to create or assist the dental treatment provider in creating orthodontic setups, dental restoration designs, dental prosthesis designs, dental implant placements, and orthognathic surgery plans.

Computing system 14 receives data indicative of an oral cavity of a patient. The oral cavity of the patient may include dentition, and more typically human dentition, such as individual teeth, quadrants, full arches, pairs of arches which may be separate or in occlusion of various types, soft tissue (e.g., gingival and mucosal surfaces of the mouth, or perioral structures such as the lips, nose, cheeks, and chin), and the like, as well as bones and any other supporting or surrounding structures. The oral cavity may include both natural structures within a mouth and artificial structures such as dental objects (e.g., prosthesis, implant, appliance, restoration, restorative component, or abutment).

Computing system 14 may receive the data indicative of the oral cavity of the patient directly in vivo using an intra-oral scanner, Cone Beam Computed Tomography (CBCT) scanning (i.e., 3D X-ray), Optical Coherence Tomography (OCT), Magnetic Resonance Imaging (MRI), or any other 3D image capturing system. In other examples, computing system 14 may receive the data indicative of the patient's oral cavity indirectly by scanning an impression of the teeth or a casting made from an impression of the teeth. Some examples of indirect data acquisition methods include, but are not limited to, industrial Computed Tomography (CT) scanning (i.e., 3D X-ray), laser scanning, and patterned light scanning. For example, computing system 14 may obtain digital images from multiple views of teeth or other intra-oral structures, and process the digital images to generate a digital 3D model or scan representing the scanned teeth or other intra-oral structure. The 3D models or scans can be implemented as, for example, a polygonal mesh or point cloud representing the surface of the scanned object or intra-oral structure.

In some examples, computing system 14 stores the data indicative of the patient's oral cavity as oral model data 26 within storage devices 22. Oral model data 26 may include digital 3D models of dentition or other intra-oral structures from intra-oral 3D scans or scans of impressions or castings of teeth. For example, oral model data 26 may include a 3D model or scan representative of the patient's dentition, such as 3D model or scan representative of the patient's mandibular arch (e.g., lower jaw and teeth) of a patient and/or a 3D model or scan representative of a maxillary arch (e.g., upper jaw and teeth) of the patient. The 3D model representative of the dentition, mandibular arch, and maxillary arch are referred to within this document as a virtual dentition, virtual mandibular arch, and virtual maxillary arch, respectively. In some examples, oral model data 26 includes scans of the patient's oral cavity for different bite poses, such as a closed (e.g., centric/maximum intercuspation) scan, open scan, forward or protrusive scan, lateral left scan, and lateral right scan.

Oral model data 26 may include a 3D virtual articulation model of the patient's oral cavity that is based on the virtual mandibular arch, the virtual maxillary arch, and/or the bite pose scans. In some examples, computing system 14 determines the virtual articulation model according to techniques described in U.S. patent application Ser. No. 15/196,631, titled "VIRTUAL MODEL OF ARTICULATION FROM INTRA-ORAL SCANS," filed Jun. 29, 2016 and incorporated by reference herein in its entirety. The 3D virtual articulation model may characterize the TMJ motion. For example, the 3D virtual articulation module may indicate a pure rotational axis of the virtual mandibular arch relative to the virtual maxillary arch.

Virtual articulation module 24 may use oral model data 26 to perform a variety of actions, such as treatment planning, crown and implant preparation, prosthodontic restorations, orthodontic setup design, orthodontic appliance design, and in diagnostic aides, for example to assess or visually illustrate tooth wear. As will be explained in more detail below, virtual articulation module 24 may use oral model data 26 to determine whether a patient's tooth is oriented or aligned correctly (e.g., to avoid interference with another tooth or to provide proper axial loading) or whether the morphology (i.e., shape) of the patient's tooth is correct (e.g., to avoid interference with another tooth). In one example, virtual articulation module 24 determines whether the tooth is oriented, positioned, or shaped correctly based on the motion of the tooth, as described below, such that when a tooth is correctly oriented, positioned, and/or shaped, the result is that the tooth avoids interference with another tooth. In another example, positioning, orienting, and/or shaping the teeth correctly may minimize tooth wear, end a bruxing habit, reduce pain or discomfort, improve mastication, improve speech, improve aesthetics, improve occlusion stability (e.g., by lowering contact forces and thus pressure on the periodontal ligaments below a threshold needed to cause tooth movement), or a combination thereof. Virtual articulation module 24 may determine whether a tooth is oriented correctly or shaped correctly based at least in part on a 3D virtual articulation model of oral model data 26. The 3D virtual articulation model may define one or more rotational axes of the virtual mandibular arch. In some examples, the 3D virtual articulation model defines four rotational axes (also referred to as pure rotational axes) associated with movement of the virtual mandibular arch from one of four different positions (e.g., open, left, right, forward). For example, each rotational axis of the four rotational axes may be indicative of a protrusive excursion, a left lateral excursion, a right lateral excursion, or an open gape excursion, of the virtual mandibular arch. Rotational axes indicative of a protrusive excursion, a left lateral excursion, a right lateral excursion, or an open gape excursion may be referred to as a protrusive guidance axis, a left guidance axis, a right guidance axis, and open gape axis, respectively.

In some examples, virtual articulation module 24 receives data indicating a selected point of a virtual dentition of the patient's oral cavity. In one example, virtual articulation module 24 outputs a graphical user interface (GUI) that includes a graphical representation of at least a portion of the patient's oral cavity, such as an image of the virtual mandibular arch and/or virtual maxillary arch. Computing system 14 may detect a user input via input device 18 (e.g., a touch input, a mouse input, etc.) selecting a particular point within the patient's oral cavity. Input device 18 may generate data indicative of the user input (e.g., data indicating a location of the GUI at which the user input was received) selecting a point on or within the dentition of the patient and may output the data indicative of the selected point to virtual articulation module 24.

In some instances, virtual articulation module 24 selects the point within or on the dentition. For instance, virtual articulation module 24 may identify one or more points in the fossa of one or more teeth, on a surface (e.g., an occlusal surface) of one or more teeth, within one or more teeth, within a respective root of one or more teeth, within the gingiva, or a combination thereof. As one example, virtual articulation module 24 may select one or more contact points by virtually articulating a 3D virtual articulation model (e.g., performing various excursions) and detecting points where collisions of the teeth occur. In some examples, virtual articulation module 24 virtually articulates the 3D model in response to receiving user input. In another example, virtual articulation module 24 virtually articulates the 3D model automatically, for example, by performing a pre-defined set of excursions. In some scenarios, virtual articulation module 24 detects one or more wear facets by identifying flat or curved surfaces in expected areas of contact and selecting a point within the wear facet as the point on the dentition.

Responsive to receiving the data indicating the selected point of the virtual dentition, virtual articulation module 24 may determine one or more tangent vectors for the selected point. Each respective tangent vector indicates a direction of motion of the selected point. In some examples, each of the tangent vectors is tangent to a circular arc centered on the respective rotational axis. In other words, as illustrated further in FIG. 5, each rotational axis defines a center of a circle or circular arc, and the selected point defines a radius of the circle or circular arc, such that each tangent vector is tangent to the circle or circular arc at the selected point. Together, the selected point and the tangent vector define a ray that has a definite position and direction in space. Without a base point, the position of the tangent vector is ambiguous. Note that at a given distance along the rotational axis, as defined by a plane normal to the axis, every point in the plane determines a different tangent vector. However, every point along a line that is parallel to the rotational axis will have the same tangent vector but a different base point. As such, every point in the space of the virtual dentition will define a unique ray. These rays may be used to determine whether a point of the virtual dentition will intersect a portion of the virtual dentition residing in the opposing arch as any of various mandibular excursions are carried out.

Virtual articulation module 24 performs one or more actions in response to determining the tangent vector. In the example of FIG. 1, virtual articulation module 24 may perform an action by outputting to display device 16 a GUI 30 that includes a graphical representation of at least a portion of the dentition (e.g., at least a portion of the virtual mandibular arch and/or virtual maxillary arch) and the tangent vector. In the example of FIG. 1, GUI 30 includes a visual representation of tooth 32 and tangent vectors 34A-34D (collectively, tangent vectors 34).

In another example, virtual articulation module 24 performs an action by determining whether a particular tooth is oriented and/or shaped correctly. Virtual articulation module 24 may determine whether the particular tooth is oriented and/or shaped correctly based on the tangent vector, e.g., using the tangent vector as a reference. For example, virtual articulation module 24 may determine whether the particular tooth is oriented or shaped correctly by determining whether one or more rays defined by a selected point and tangent vectors 34 intersects a surface (e.g., an occlusal surface) of the particular tooth. In some examples, a ray defined by a selected point and tangent vector 34 that intersects a surface of the particular tooth may indicate that the portion of the particular tooth will interfere with a portion of an antagonist tooth. As a result, virtual articulation module 24 may determine that the particular tooth is not oriented correctly, is not shaped correctly, or both. In other words, virtual articulation module 24 may determine whether the particular tooth is oriented and shaped properly to reduce or prevent interference with another tooth (e.g., an antagonist tooth) by determining whether one of the rays defined in part by tangent vectors 34 intersects a surface (e.g., an occlusal surface) of the particular tooth.

In yet another example, virtual articulation module 24 may perform an action by determining whether the particular tooth is oriented correctly for axial loading of the particular tooth. For example, the selected point may lie on a surface of a root of the particular tooth, or within the root, and virtual articulation module 24 may determine whether the root is oriented properly to transfer loads or forces on the tooth to the bone. As one example, virtual articulation module 24 determines whether the root is oriented properly by determining whether the tangent vector is substantially parallel to the root of the tooth. In some instances, when the root of the tooth is not oriented properly, forces on the tooth may cause the tooth to move (e.g., over time), which may cause interference with an antagonist tooth and possibly wear on the tooth or its antagonist.

In some examples, virtual articulation module 24 updates or modifies oral model data 26. For example, virtual articulation module 24 may modify the dentition by updating an orientation, position, and/or shape of one or more teeth. For instance, virtual articulation module 24 may modify an orientation of one or more teeth by changing a torque angle of the respective tooth. In another instance, virtual articulation module 24 may modify a shape of one or more teeth by adding and/or removing material from the respective tooth. In yet another instance, virtual articulation module 24 may modify a position of a tooth, for example, by translating a tooth in a mesio-distal direction to achieve a Class I molar relationship or translating a tooth in a bucco-lingual direction to resolve a posterior crossbite. As another example, virtual articulation module 24 may update or modify oral model data 26 in response to receiving a user input from the dental treatment provider via input device 18 to modify the orientation, shape, or both of one or more teeth.

Responsive to modifying oral model data 26, virtual articulation module 24 may determine whether, in the arrangement of virtual dentition the modified oral model data 26, one or more teeth are oriented and/or shaped correctly based on the modified oral model data 26. For example, virtual articulation module 24 may determine one or more tangent vectors for one or more points on the updated dentition. In such examples, virtual articulation module 24 may determine whether one or more modified virtual teeth of the modified dentition are oriented and/or shaped correctly by determining whether any of the rays defined by a selected point and the associated tangent vectors intersect an occlusal surface of the modified virtual tooth or teeth. As another example, virtual articulation module 24 may determine whether a modified virtual tooth is oriented correctly by determining whether the tangent vector is aligned (e.g., substantially parallel) with the virtual root of the particular virtual tooth.

In this way, a computing device may determine the correct orientation and/or shape of any tooth in the patient's oral cavity based on the patient's own mandibular dynamics. For example, using the patient's own mandibular dynamics, the computing device may determine the correct orientation and/or shape of the patient's tooth or teeth within a single arch irrespective of a shape or orientation of a tooth or teeth in the opposing arch. Determining the correct position, orientation, and shape of a tooth may enable a computing device or dental treatment provider to create a treatment plan that reduces or eliminates interference between the patient's teeth. Reducing or eliminating interference between teeth may prolong dental health and improve quality of life of the patient.

Figure 2:
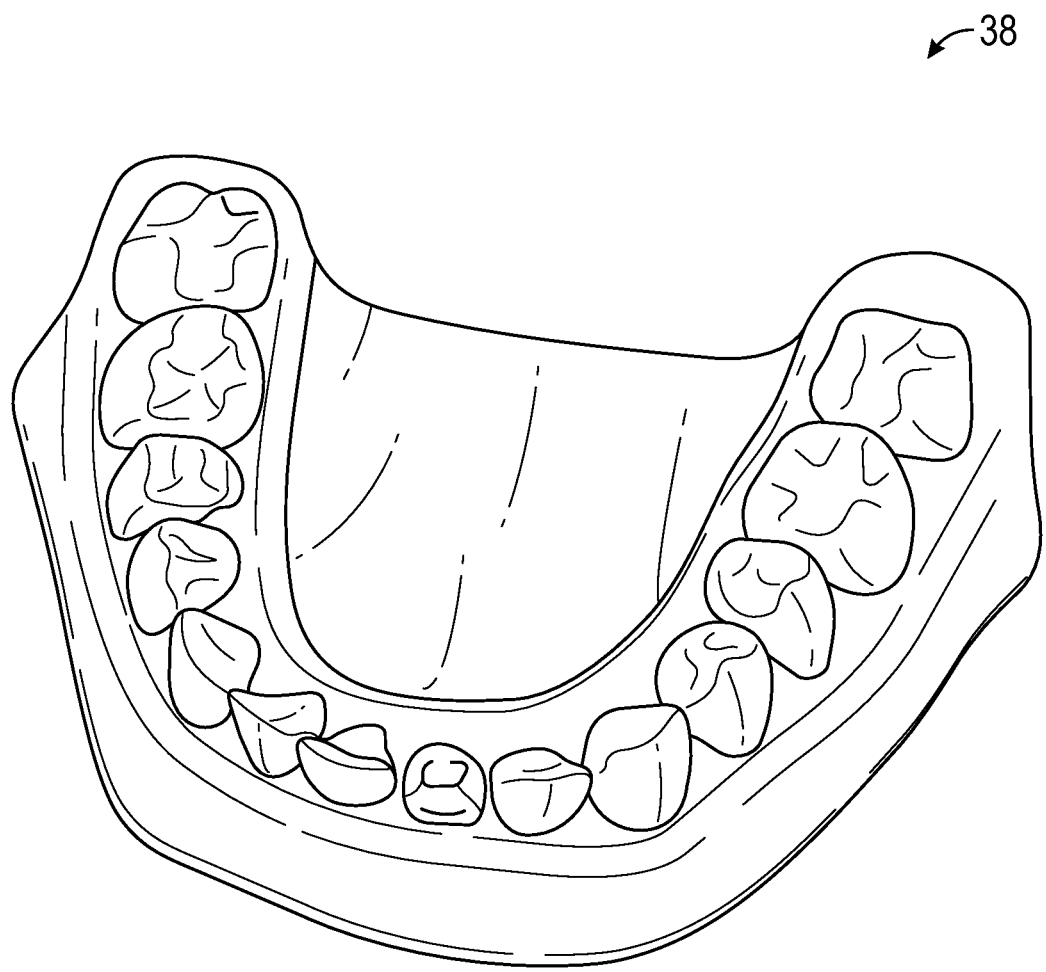
FIG. 2 illustrates an example of a digital 3D model of a patient's teeth, according to one example of the disclosure.

FIG. 2 illustrates an example of a digital 3D model of a patient's teeth, according to one example of the disclosure. As illustrated in FIG. 2, oral model data 26 includes a virtual mandibular arch 38 representing the patient's mandibular arch. Oral model data 26 may include a virtual maxillary arch representing the patient's maxillary arch.

Figure 3:
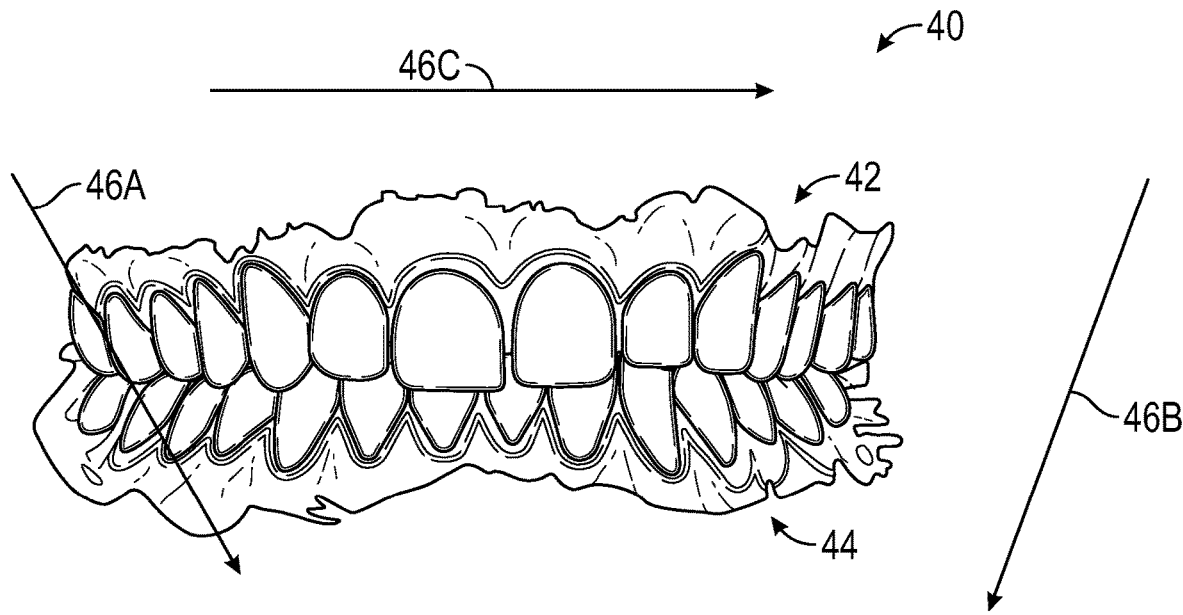
FIG. 3 illustrates a facial view of an example digital 3D model of dental arches posed in maximum intercuspation, according to one example of the disclosure.

FIG. 3 illustrates a facial view of an example digital 3D model of dental arches posed in maximum intercuspation, according to one example of the disclosure. FIG. 3 is described with reference to system 10 of FIG. 1. Digital 3D model 40 includes virtual maxillary arch 42 and virtual mandibular arch 44. Each of rotational axes 46A-46C (collectively, rotational axes 46) is associated with motion of virtual mandibular arch 44 in a respective direction of a plurality of different directions. In the example of FIG. 3, rotational axis 46A may indicate the right guidance of virtual mandibular arch 44, rotational axis 46B may indicate the left guidance of virtual mandibular arch 44, and rotational axis 46C may indicate the open gape of virtual mandibular arch 44. In some examples, rotational axes 46A and 46B (e.g., lateral guidance axes) do not necessarily pass through definite anatomical features of the virtual dentition. For example, rotational axes 46A and 46B comprise two rotations, such as one rotation for a lateral excursion and one rotation for an open gape.

Figure 4:
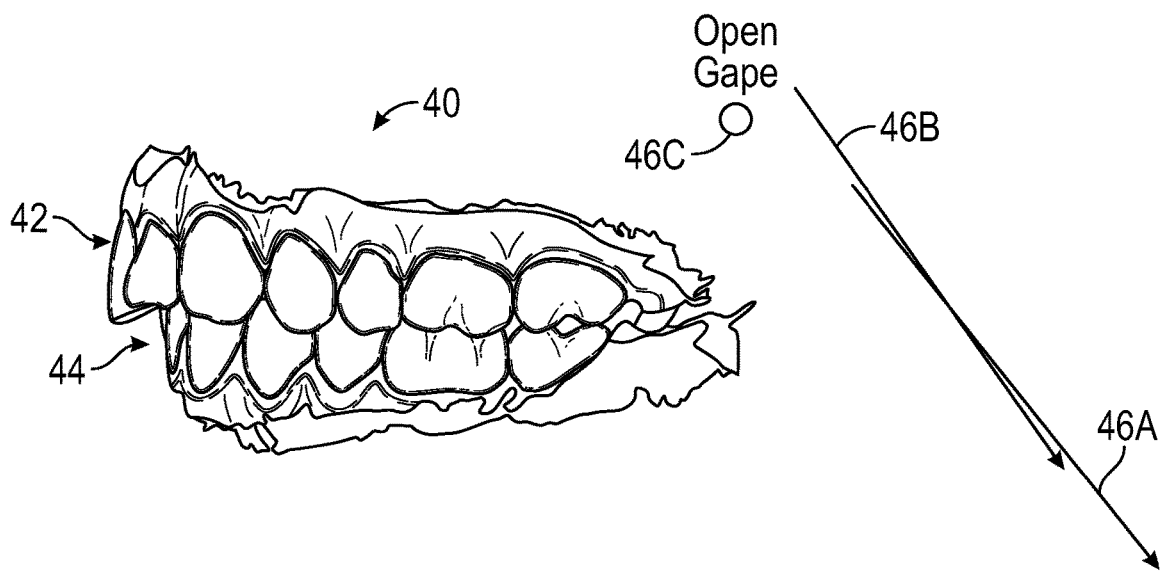
FIG. 4 illustrates left lateral view of a digital 3D model of dental arches posed in maximum intercuspation, according to one example of the disclosure.

FIG. 4 illustrates a left lateral view of an example digital 3D model of dental arches posed in maximum intercuspation, according to one example of the disclosure.

Figure 5:
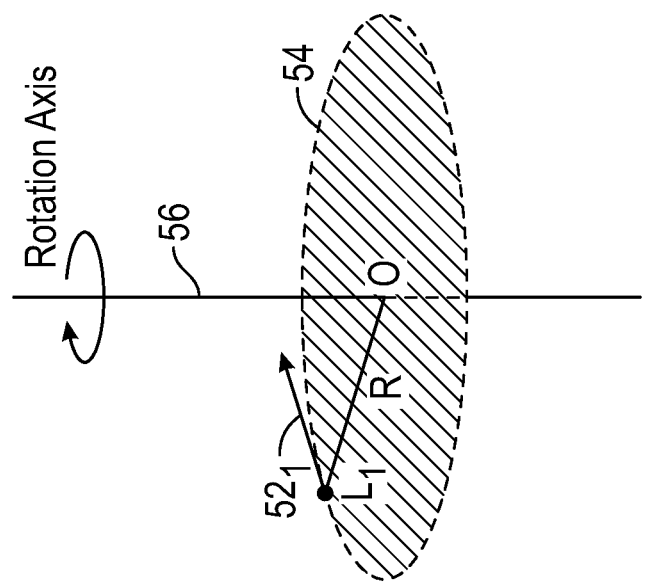
FIG. 5 illustrates an example rotational axis and example tangent vectors or rays, according to one example of the disclosure.
Figure 5:
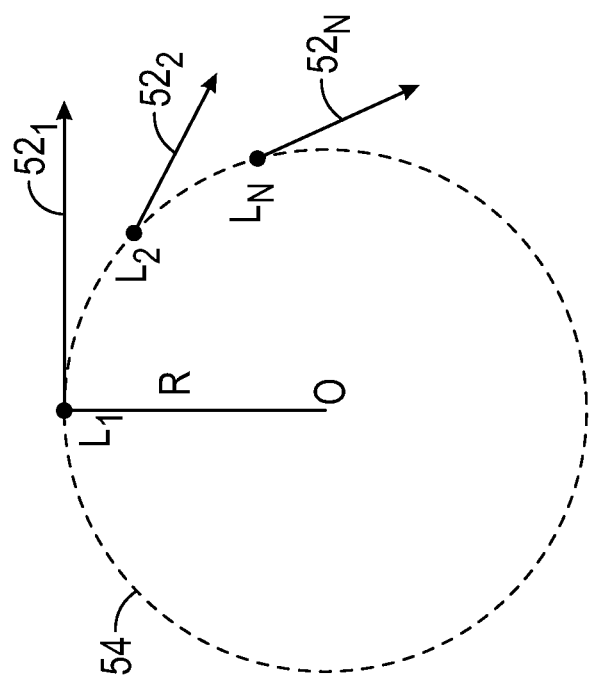

FIG. 5 illustrates an example rotational axis and example tangent vectors or rays, according to one example of the disclosure. FIG. 5 is described with reference to system 10 of FIG. 1. Virtual articulation module 24 may calculate one or more tangent vectors $52_1$-$52_N$ (collectively, tangent vectors 52). Tangent vector $52_1$ indicates an initial direction of motion of a selected point at a location $L_1$. Tangent vector 52 is tangent to a circle 54 (or a portion of a circle, such as a circular arc) centered on rotational axis 56. The plane of circle 54 is perpendicular to rotational axis 56. In this way, rotational axis 56 defines a center of circle 54 (or a circular arc), and the location $L_1$ defines a radius R of the circle or circular arc, such that tangent vector 52 is tangent to the circle 54 or circular arc at location $L_1$. Together, each selected point $L_1$ and its associated tangent vector $52_i$ define a ray that has a definite position and direction in space. Without a base point, the position of tangent vector $52_i$ is ambiguous. Note that at a given distance along the rotational axis, as defined by a plane normal to the axis, every point in the plane determines a different tangent vector. However, every point along a line that is parallel to the rotational axis will have the same tangent vector but a different base point. As such, every point in the space of the virtual dentition will define a unique ray. These rays may be used to determine whether a point of the virtual dentition will intersect a portion of the virtual dentition residing in the opposing arch as any of various mandibular excursions are carried out. Virtual articulation module 24 may re-calculate tangent vectors for a plurality of locations along circular arc 54 (also referred to as a guidance path). For instance, virtual articulation module 24 may calculate tangent vector $52_1$ at point $L_1$ and re-calculate new tangent vectors $52_2$-$52_N$ at locations $L_2$-$L_N$.

Figure 6:
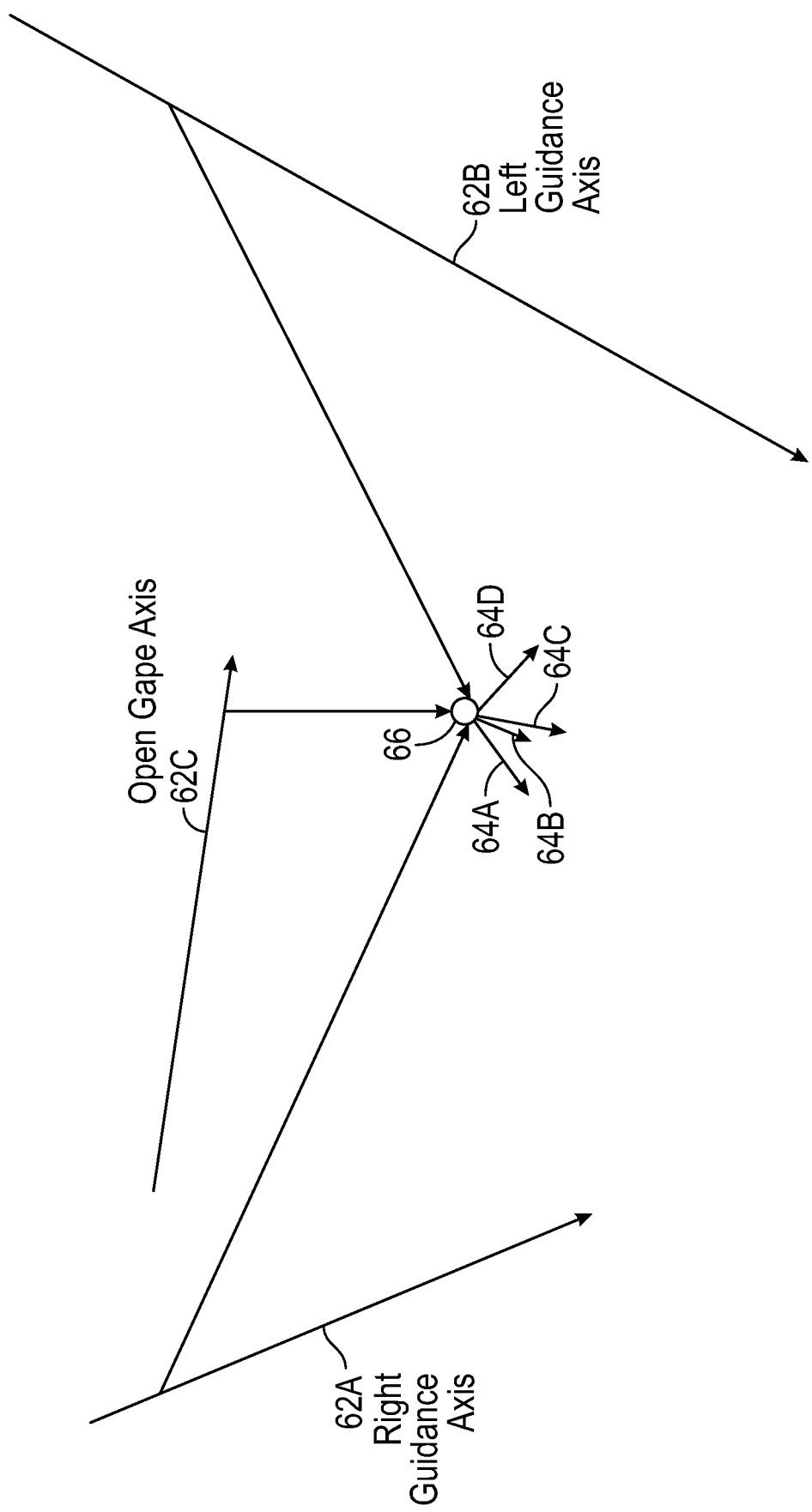
FIG. 6 illustrates rotational axes and tangent vectors or rays, according to one example of the disclosure.

FIG. 6 illustrates example rotational axes and tangent vectors, or rays, according to one example of the disclosure. FIG. 6 is described with reference to system 10 of FIG. 1. Virtual articulation module 24 may determine a plurality of rotational axes 62A-62C (collectively, rotational axes 62) and a plurality of tangent vectors 64A-64D (collectively, tangent vectors 64). Note that point 66 and each of tangent vectors 64 defines a ray having a definite position and direction in the space of the virtual dentition. In the example of FIG. 6, rotational axes 62A may be a right guidance axis, rotational axes 62B may be a left guidance axis, and rotational axes 62C may be an open gape axis. Each of tangent vectors 64 indicates an initial direction of motion of point 66 for a respective excursion. For example, tangent vectors 64A, 64B, 64C, and 64D each indicate an initial direction of point 66 for a right lateral excursion, a protrusive excursion, an open gape excursion, and a left lateral excursion, respectively.

Figure 7:
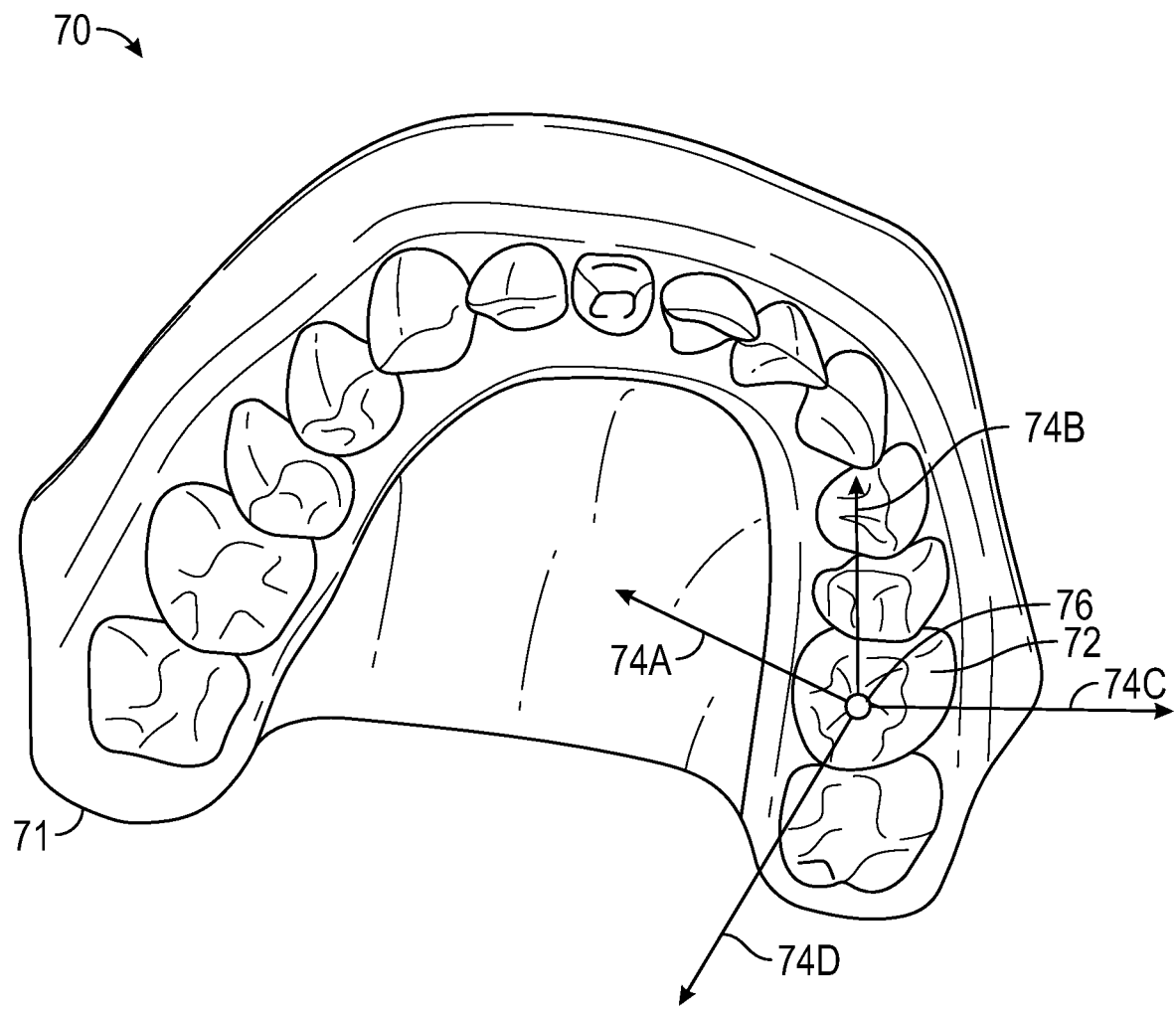
FIG. 7 illustrates an example dental arch and a plurality of tangent vectors or rays, according to one example of the disclosure.

FIG. 7 illustrates an example dental arch and a plurality of tangent vectors or rays, according to one example of the disclosure. FIG. 7 is described with reference to system 10 of FIG. 1. Virtual maxillary arch 71 includes tooth 72.

Virtual articulation module 24 may receive an indication of a user input selecting point 76, or it may select point 76 on the surface of tooth 72. In the example of FIG. 7, point 76 is associated with a wear facet of tooth 72. Virtual articulation module 24 may determine a plurality of tangent vectors 74A-74D (collectively, tangent vectors 74) associated with point 76. Point 76 and each of tangent vectors 74 defines a ray having a definite position and direction in the space of the virtual dentition. Tangent vectors 74A, 74B, 74C, and 74D may indicate an initial direction of point 76 for a right lateral excursion, a protrusive excursion, a left lateral excursion, and an open gape excursion, respectively.

Figure 8:
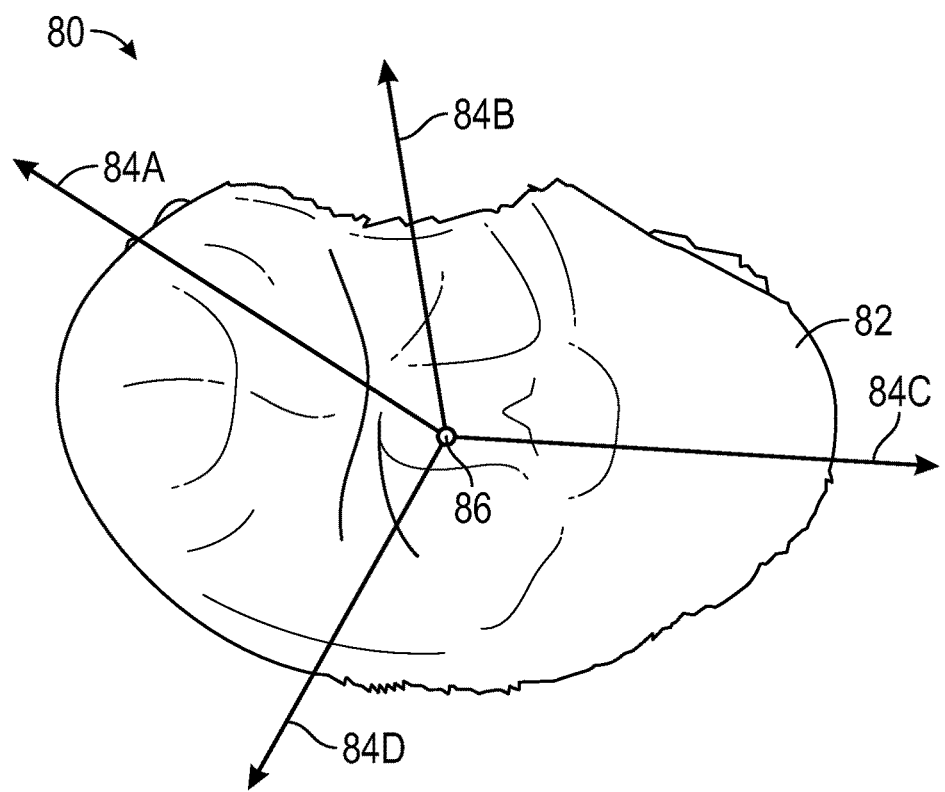
FIG. 8 illustrates an example user interface of an occlusal view of a tooth and a plurality of tangent vector or rays, according to one example of the disclosure.

FIG. 8 illustrates an example user interface, according to one example of the disclosure. FIG. 8 is described with reference to system 10 of FIG. 1. Virtual articulation module 24 may output GUI 80 for display by display device 16. In some examples, GUI 80 includes graphical representation of at least a portion of the virtual dentition, such as a graphical representation of a particular tooth 82.

Virtual articulation module 24 may receive an indication of a user input selecting point 86, or may select point 86 on the surface of tooth 82. In the example of FIG. 8, point 86 is associated with a wear facet of tooth 82. Virtual articulation module 24 may determine a plurality of tangent vectors 84A-84D (collectively, tangent vectors 84) associated with point 86. Similarly, virtual articulation module 24 may determine a plurality of rays defined by tangent vectors 84 and point 86. GUI 80 output by virtual articulation module 24 may include graphical representations for each of tangent vectors 84, point 86, or rays defined therefrom. Tangent vectors 84A, 84B, 84C, and 84D may indicate an initial direction of point 86 for a right lateral excursion, a protrusive excursion, a left lateral excursion, and an open gape excursion, respectively.

Figure 9:
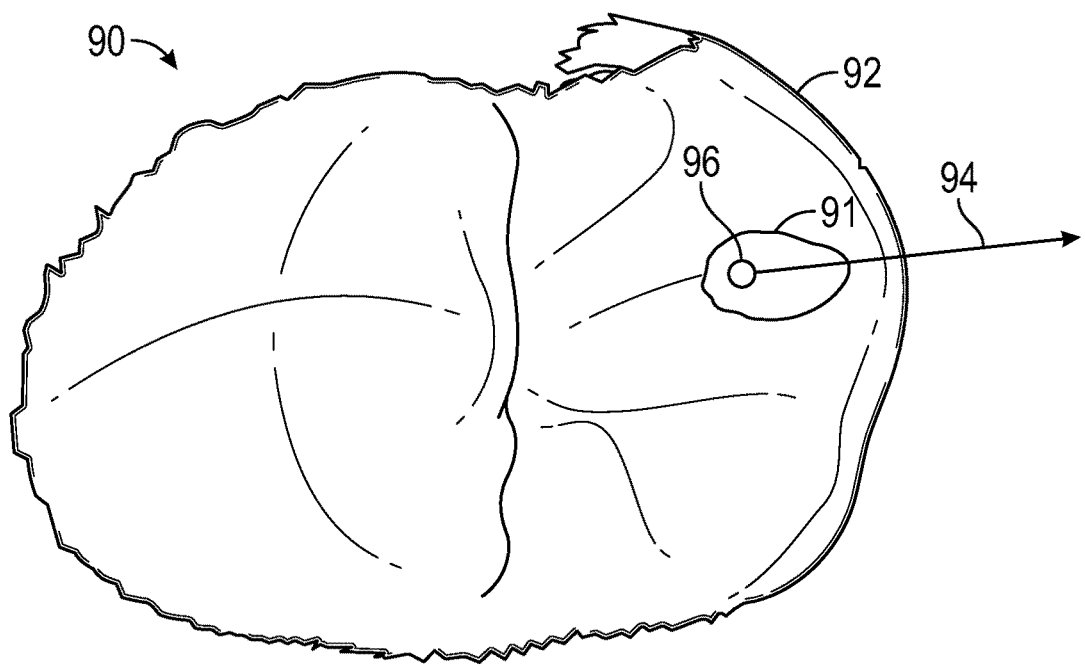
FIG. 9 illustrates an example user interface of an occlusal view of a tooth and a tangent vector or ray, according to one example of the disclosure.

FIG. 9 illustrates an example user interface according to one example of the disclosure. FIG. 9 is described with reference to system 10 of FIG. 1. Virtual articulation module 24 may output GUI 90 for display by display device 19. In some examples, GUI 90 includes graphical representation of at least a portion of the virtual dentition, such as a graphical representation of a particular tooth 92.

Virtual articulation module 24 may receive an indication of a user input selecting point 96, or it may select point 96 on the surface of tooth 92. In the example of FIG. 9, point 96 is associated with a wear facet 91 of tooth 92. In the example of FIG. 9, wear facet 91 is located on the lingual side of the buccal cusp of tooth 92. Wear facet 91 may be located at any location of tooth 92 where tooth 92 contacts an antagonist tooth. Virtual articulation module 24 may determine one or more tangent vectors 94 associated with a selected point 96 within wear facet 91. In the example of FIG. 9, tangent vectors 94 may indicate an initial direction of point 96 for a left lateral excursion.

In some examples, virtual articulation module 24 identifies a direction of motion that caused wear facet 91 based on a tangent vector associated with wear facet 91 (e.g., tangent vector 94). For example, virtual articulation module 24 may determine one or more tangent vectors associated with point 96 within wear facet 91. In the example of FIG. 9, GUI 90 include tangent vector 94 associated with point 96. Virtual articulation module 24 may determine the direction of motion that caused wear facet 91 by determining whether any of the tangent vectors associated with point 96 are substantially parallel to the surface of wear facet 91. For instance, when tangent vector 94 associated with point 96 is substantially parallel to the plane of wear facet 91, this may indicate that motion in the direction of tangent vector 94 (e.g., a left lateral excursion) caused premature contact between wear facet 91 of tooth 92 and an antagonist tooth in the opposing arch, thus creating wear facet 91 over an extended period of time. In one scenario, virtual articulation module 24 determines that tangent vector 94 is substantially parallel to the plane of wear facet 91. In response to determining that tangent vector 94 is substantially parallel to the plane of wear facet 91, virtual articulation module 24 may determine that the direction of motion associated with tangent vector 94 is the direction of motion that caused wear facet 91. In such scenarios, virtual articulation module 24 determines wear facet 91 was caused by a left lateral excursion.

In one example, virtual articulation module 24 may determine whether wear facet 91 is an active wear facet based on tangent vector 94. An active wear facet may refer to a wear facet that continues to wear during motion of the patient's TMJ. An inactive wear facet may refer to a previously created wear facet that no longer wears during motion of the patient's TMJ (for example, a wear facet that was caused prior to receiving dental treatment, such as orthodontic braces). In some examples, virtual articulation module 24 may determine that the wear facet is an active wear facet in response to determining that tangent vector 94 is substantially parallel to the plane of wear facet 91.

In another example, virtual articulation module 24 may determine that wear facet 91 is an inactive wear facet in response to determining that the plane of wear facet 91 is not substantially parallel to tangent vector 94. For example, the wear might have occurred prior to orthodontic treatment while the patient had a malocclusion. After orthodontic treatment, the wear facets on the teeth might be in different orientations relative to the tangent vectors of motion that originally created them. In such situations, virtual articulation module 24 may determine that wear facet 91 is an inactive wear facet, which may indicate that the problem which created the facets has been resolved.

Figure 10A:
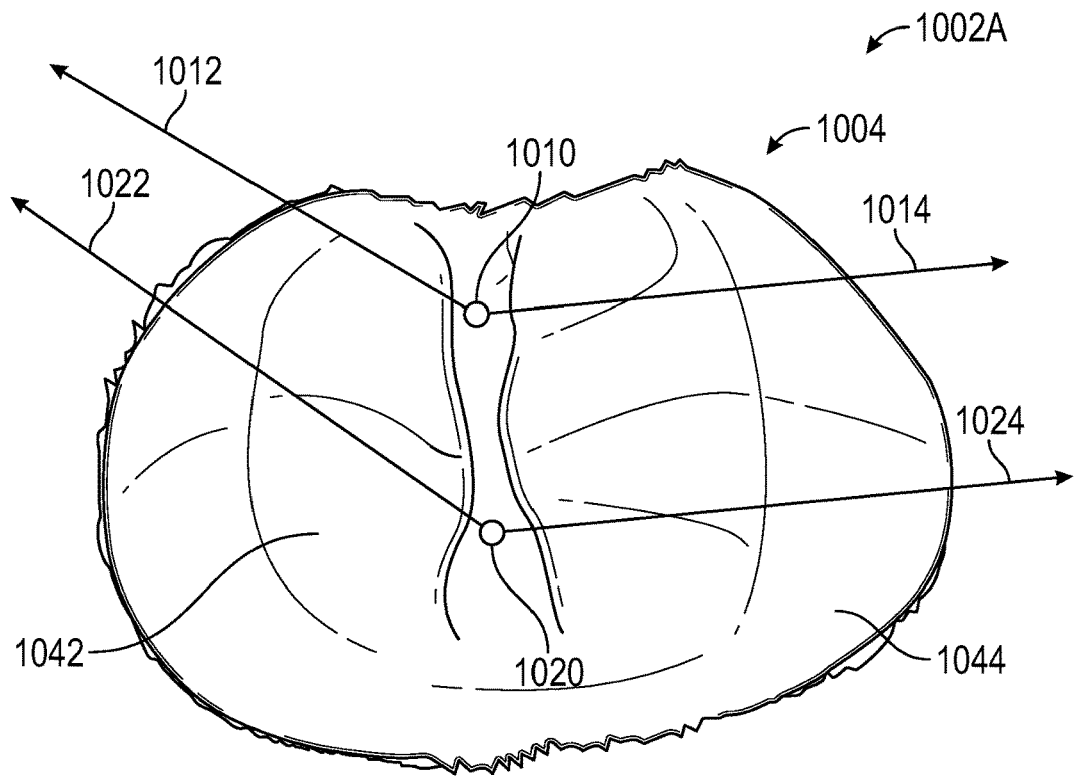
FIGS. 10A and 10B illustrate example user interfaces of a tooth and a plurality of tangent vectors or rays, according to one example of the disclosure.
Figure 10B:
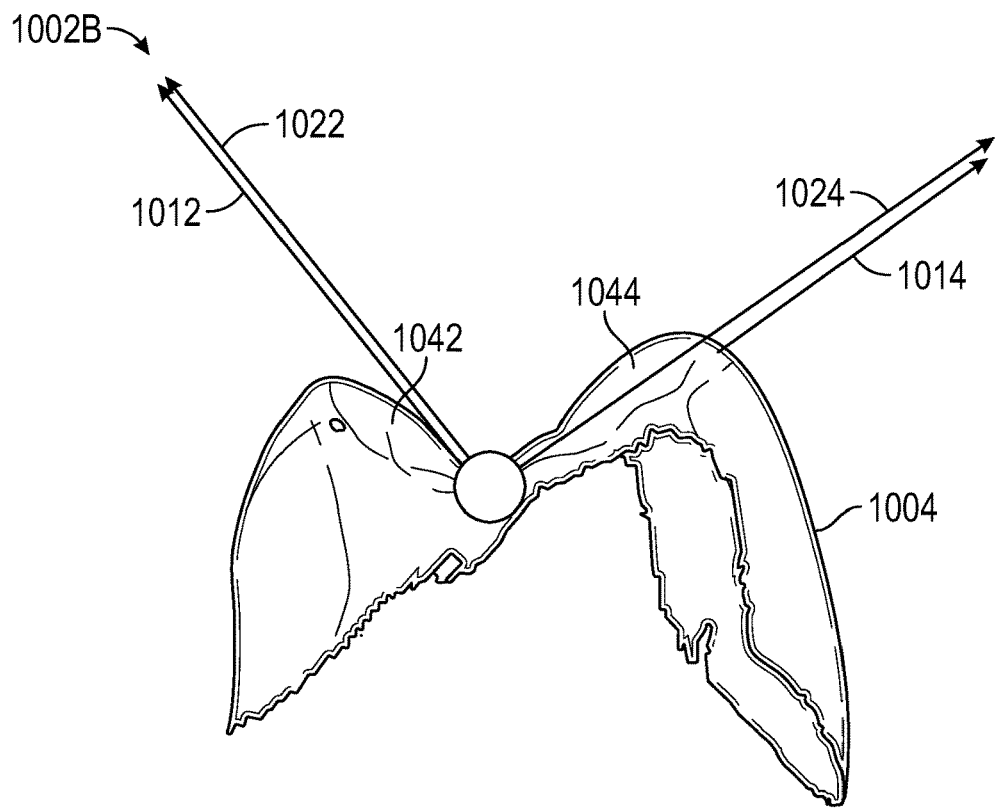

FIG. 10A illustrates an example user interface 1002A according to one example of the disclosure. FIG. 10B illustrates an example user interface 1002B according to one example of the disclosure. FIGS. 10A and 10B (collectively, FIG. 10) are described with reference to system 10 of FIG. 1. GUIs 1002A and 1002B (collectively, GUIs 1000) illustrate atop view (e.g., an occlusal surface) of tooth 1004 and a side view (e.g., a distal surface) of tooth 1004, respectively.

As illustrated in FIG. 10A, GUI 1002A includes graphical representations of points 1010, 1020, and 1030. As illustrated in FIGS. 10A and 10B, GUIs 1002 include graphical representations of tangent vectors 1012 and 1014 associated with point 1010. Similarly, GUIs 1002 may include graphical representations of tangent vectors 1022 and 1024 associated with point 1020, together defining rays having a definite position and directions in the space of the virtual dentition. In some instances, points 1010, 1020 are selected by a user. In another instance, virtual articulation module 24 may select points 1010 and 1020 located within the fossa of tooth 1004. In the example of FIG. 10, tangent vectors 1012 and 1022 are associated with a right lateral excursion and tangent vectors 1014 and 1024 are associated with a left lateral excursion.

Virtual articulation module 24 may determine whether the orientation and/or shape of tooth 1004 is correct based at least in part on one or more of tangent vectors 1012, 1014, 1022, or 1024.

According to one example, virtual articulation module 24 determines whether the orientation (e.g., torque angle) of tooth 104 by determining whether one of the rays defined by tangent vectors 1012, 1022 and points 1010, 1020, respectively, intersects a surface of lingual cusp 1042 or whether one of the rays defined by tangent vectors 1014, 1024 and the same points 1010, 1020, respectively, intersect a surface of buccal cusp 1044 of tooth 1004. In the example of FIG. 10B, virtual articulation module 24 determines that tooth 1004 is not oriented correctly (e.g., the current torque angle will cause tooth 1004 to interfere with an antagonist tooth) in response to determining whether one or both of the rays defined in part by tangent vectors 1014, 1024 intersect a surface of buccal cusp 1044.

When the orientation of tooth 1004 is not correct, as illustrated in the example of FIG. 10B, a lateral left excursion may result in premature contact of buccal cusp 1044 with a surface of an antagonist tooth, as can be seen by the rays associated with left lateral tangent vectors intersecting this region of the tooth, and the existence of a wear facet 1031. In the example of FIG. 10B, a right lateral excursion will be devoid of contact along the lingual cusp 1042 because the right lateral tangent vectors 1012 and 1022 are sloped away from cusp 1042. In such examples, virtual articulation module 24 may determine a torque angle for the tooth, as further described below with reference to FIGS. 11A and 11B.

Figure 11A:
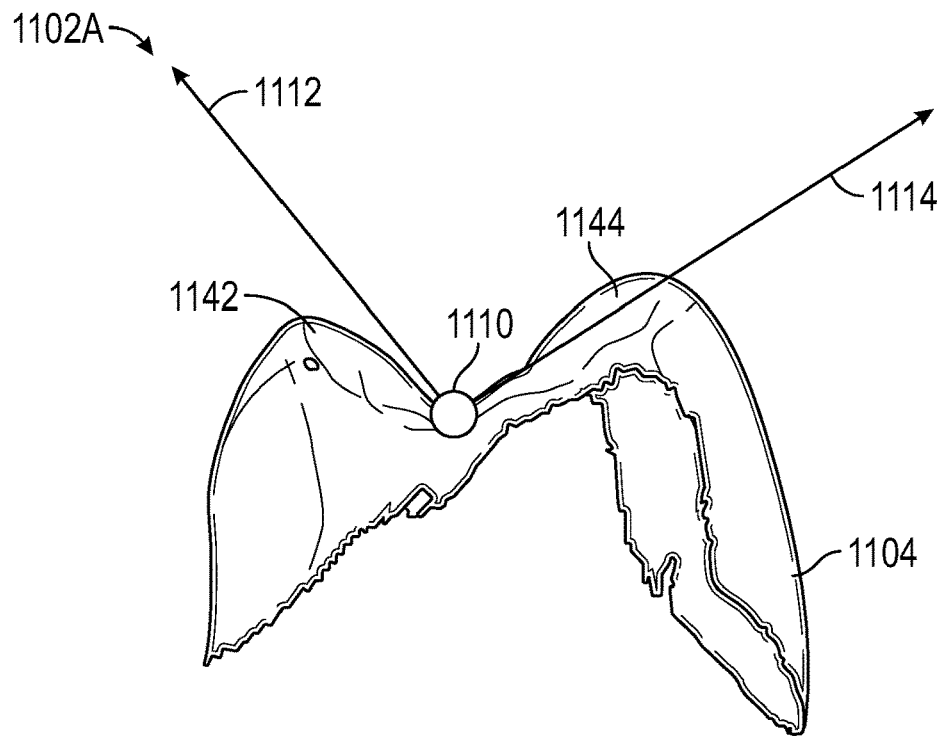
FIGS. 11A and 11B illustrate example user interfaces of a distal view of a tooth and a plurality of tangent vectors or rays, according to one example of the disclosure.
Figure 11B:
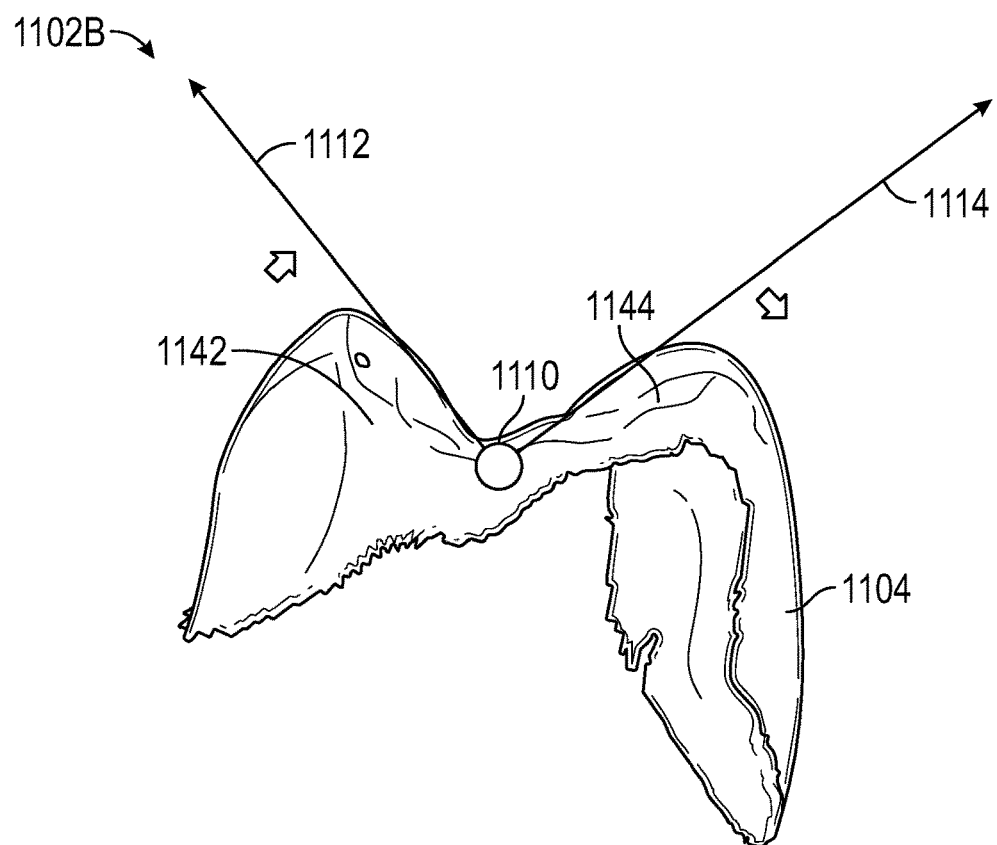

FIG. 11A illustrates an example user interface 1102A according to one example of the disclosure. FIG. 11B illustrates an example user interface 1102B according to one example of the disclosure. FIGS. 11A and 11B (collectively, FIG. 11) are described with reference to system 11 of FIG. 1. GUIs 1102A and 1102B (collectively, GUIs 1100) illustrate a side view (e.g., a distal surface) of tooth 1104, respectively.

As illustrated in FIG. 11, GUIs 1102 each include a graphical representation of point 1110, along with tangent vectors 1112 and 1114 associated with point 1110, together defining rays having a definite position and directions in the space of the virtual dentition. In some examples, virtual articulation module 24 may select point 1110 within the fossa of tooth 1104. In the example of FIG. 11, tangent vector 1112 is associated with a right lateral excursion, and tangent vector 1114 is associated with a left lateral excursion.

Virtual articulation module 24 may determine whether the orientation and/or shape of tooth 1104 is correct based at least in part on one or more of tangent vectors 1112 and/or 1114. In some examples, virtual articulation module 24 may determine whether the orientation of tooth 1104 is correct by determining whether the rays defined by tangent vectors 1112 and point 1110 intersects a surface of lingual cusp 1142 or whether the ray defined by tangent vector 1114 and point 1110 intersects a surface of buccal cusp 1144. In the example of FIG. 11A, virtual articulation module 24 may determine that the orientation of tooth 1104 is not correct in response to determining that the rays defined in part by tangent vector 1114 intersects a surface of cusp 1144.

As illustrated in FIG. 11B, virtual articulation module 24 may modify or adjust the virtual dentition in response to determining the current orientation and/or shape of tooth 1104 is not correct. For example, virtual articulation module 24 may determine the proper orientation (e.g., torque angle) for one or more teeth by virtually rotating tooth 1104 about a mesio-distal axis. In one example, virtual articulation module 24 rotates tooth 1104 about the mesio-distal axis in predetermined increments (e.g., 1 degree). In another example, virtual articulation module 24 may rotate tooth 1104 in adjustable increments (e.g., based on a user input to rotate tooth 1104).

In yet another example, virtual articulation module 24 may determine a rotation angle to correct the orientation of tooth 1104. For example, virtual articulation module 24 may determine an angular difference between the orientation of a tooth surface (e.g., a surface of cusp 1142) and an associated tangent vector (e.g., tangent vector 1112). In one example, virtual articulation module 24 rotates tooth 1104 about the mesio-distal axis by the angular difference.

In some scenarios, a particular tooth (e.g., a bicuspid or molar, such as tooth 1104) includes multiple cusps. In such scenarios, virtual articulation module 24 may determine a rotation angle based on a plurality of tangent vectors and associated tooth surfaces. For example, virtual articulation module 24 may compute a mean vector between the tangent vectors 1112 and 1114, compute a mean surface plane between the surfaces of cusps 1142, 1144, and compute the angular difference in orientation between the mean tangent vector and the mean surface plane. Virtual articulation module 24 may rotate tooth 1104 by the angular difference.

Virtual articulation module 24 may determine whether the updated or modified orientation of tooth 1104 is correct by determining whether either of the rays defined by tangent vectors 1112 or 1114 and point 1110 intersect the surface of cusps 1142, 1144 after virtually rotating tooth 1104 about the mesio-distal axis. In some examples, virtual articulation module 24 determines that the updated orientation of tooth 1104 is correct in response to determining that the rays defined in part by tangent vectors 1112, 1114 do not intersect the surfaces of cusps 1142, 1144. In some examples, virtual articulation module 24 outputs GUI 1102B to indicate the correct orientation of tooth 1104.

In some examples, the paths traced by these reference points on the posterior teeth are geometrically similar to the paths traced by the canine or anterior guidance. For example, as one of reference points (e.g., point 1110) get closer to the rotational axes, the amplitude of the paths is scaled in proportion to the distances from the rotational axes. In some examples, virtual articulation module 24 may receive a user input correcting the orientation of tooth 1104. In another example, virtual articulation module 24 may receive a user input adjusting one or more guidance teeth. Virtual articulation module 24 may recalculate the rotational axes as described with respect to FIG. 20 and output a GUI illustrating the updated tangent vectors or rays and updated orientation of tooth 1104.

Virtual articulation module 24 may determine one or more treatment plans. In one example, virtual articulation module 24 may determine the correct orientation (and/or shape) for a plurality of teeth within the virtual dentition. For example, virtual articulation module 24 may determine an orthodontic treatment plan (e.g., orthodontic appliances, such as braces or retainers) to correct the orientation of one or more teeth of the maxillary and/or mandibular arch. In some examples, the orthodontic treatment plan may indicate the final, correct orientation for one or more teeth and intermediate orientations of the respective teeth to arrive at the correct orientation. In one example, the treatment plan may include a virtual model of one or more of the dental arches (e.g., to create dentures or dental implants). As another example, while virtual articulation module 24 is described as modifying the virtual dentition by adjusting an orientation of a tooth or adjusting a shape of the tooth, virtual articulation module 24 may determine a treatment plan to adjust a shape and/or orientation of a tooth, a bone, or a root of the tooth via orthognathic surgery, or by cutting the bone of the maxilla or mandible and changing the position of an entire segment of the dental arch.

While the example of FIG. 11 is described with reference to the tangent vectors associated with left and right lateral excursions to determine proper tooth orientation (e.g., proper or correct torque angle), in some examples, virtual articulation module 24 may utilize tangent vectors associated with protrusive mandibular motions along the anterior guidance to determine whether the posterior teeth are oriented or shaped correctly (e.g., assuming proper anterior guidance). As another example, virtual articulation module 24 may utilize tangent vectors to determine whether the shape and/or orientation of the canines or incisors is correct (or to determine which shape/orientation is correct). Furthermore, the shapes of the canines or incisors can be modified to achieve proper guidance, and thus protection of the posterior teeth to reduce or eliminate interference between teeth.

In this way, techniques of this disclosure may enable a computing system to determine whether the current orientation and/or shape of one or more of a patient's teeth is correct. Additionally, or alternatively, the computing system may determine the correct orientation and/or shape of the patient's teeth and output information (e.g., to a dental treatment provider) to enable a dental treatment provider to develop a treatment plan. In some examples, the computing system determines the proper torque and tip angles for bicuspids and molars, aspects of proper canine relationship, and aspects of proper incisor relationship (e.g., including proclination angles).

Figure 12A:
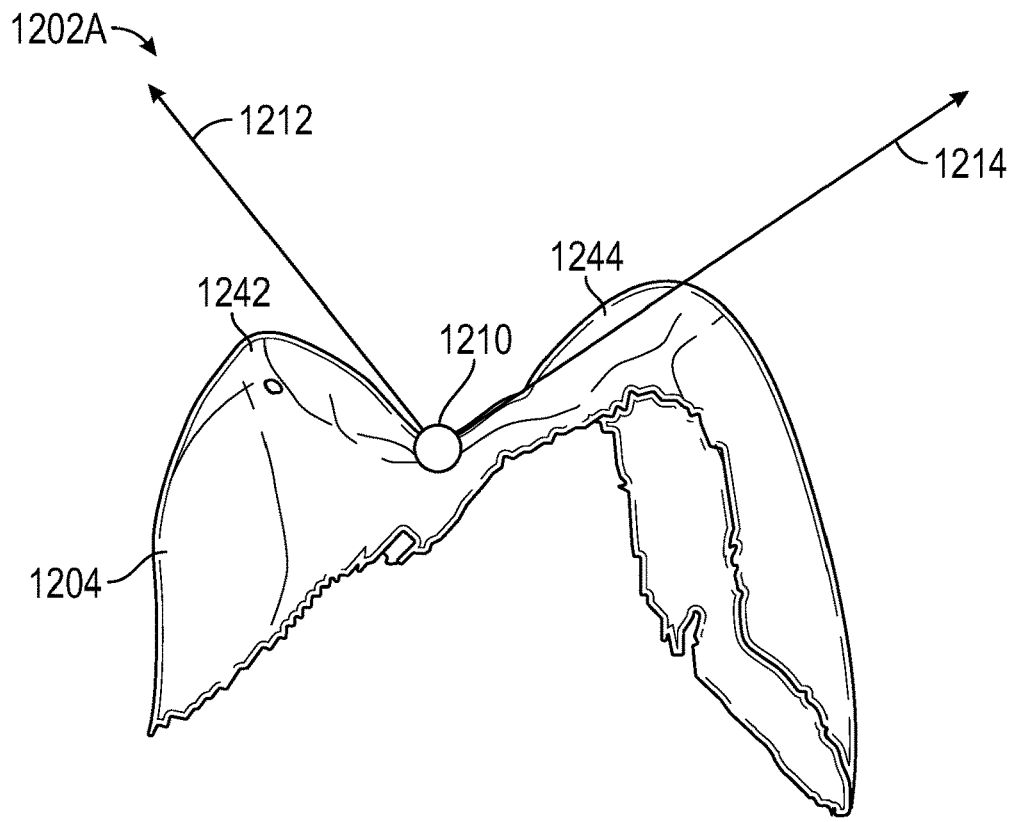
FIGS. 12A and 12B illustrate example user interfaces of a distal view of a tooth and a plurality of tangent vectors or rays, according to one example of the disclosure.
Figure 12B:
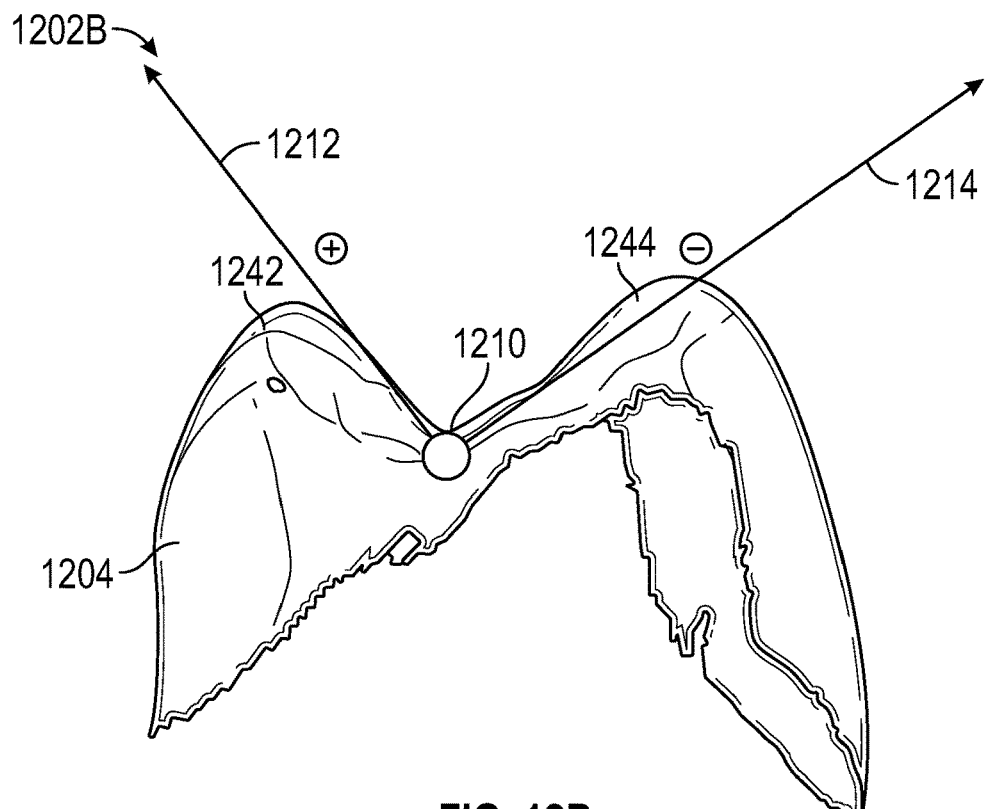

FIG. 12A illustrates an example user interface 1202A according to one example of the disclosure. FIG. 12B illustrates an example user interface 1202B according to one example of the disclosure. FIGS. 12A and 12B (collectively, FIG. 12) are described with reference to system 12 of FIG. 1. GUIs 1202A and 1202B (collectively, GUIs 1200) illustrate a side view (e.g., a distal surface) of tooth 1204, respectively.

As illustrated in FIG. 12, GUIs 1202 each include a graphical representation of points 1210. As illustrated in FIG. 12, GUIs 1202 include graphical representations of tangent vectors 1212 and 1214 associated with point 1210. Together, tangent vectors 1212, 1214 and point 1210 define rays having a definite position and directions in the space of the virtual dentition. In some examples, virtual articulation module 24 may select point 1210 within the fossa of tooth 1204. In the example of FIG. 12, tangent vector 1212 is associated with a right lateral excursion and tangent vector 1214 is associated with a left lateral excursion.

Virtual articulation module 24 may determine whether the orientation and/or shape of tooth 1204 is correct based at least in part on one or more of tangent vectors 1212 and/or 1214. In some examples, virtual articulation module 24 may determine whether the shape of tooth 1204 is correct based at least in part on a tangent vector associated with a lateral excursion (e.g., one of tangent vectors 1212 or 1214). For example, virtual articulation module 24 may determine the shape of tooth 1204 is incorrect in response to determining that the ray defined by tangent vector 1212 and point 1210 intersects a surface of lingual cusp 1242 or that the ray defined by tangent vector 1214 and point 1210 intersects a surface of buccal cusp 1244. As another example, virtual articulation module 24 may determine that the shape of tooth 1204 is incorrect in response to determining that the surfaces of cusps 1242, 1244 are not centered within the rays defined in part by tangent vectors 1212, 1214.

According to some examples, virtual articulation module 24 may modify or adjust the virtual dentition in response to determining that the current orientation and/or shape of tooth 1204 is not correct. For example, virtual articulation module 24 may adjust a shape of tooth 1204 by adding and/or removing material from tooth 1204. For example, virtual articulation module 24 may add material to one portion of tooth 1204 and remove material from another portion of tooth 1204. Virtual articulation module 24 may determine whether the updated or modified shape of tooth 1204 is correct by determining whether the ray defined by tangent vector 1212 and point 1210 intersects a surface of lingual cusp 1242 or whether the ray defined by tangent vector 1214 and point 1210 intersects a surface of buccal cusp 1244.). In some examples, virtual articulation module 24 outputs GUI 1202B to indicate the correct shape of tooth 1204.

Virtual articulation module 24 may determine one or more treatment plans. In one example, virtual articulation module 24 may determine the correct shape (and/or orientation) for a plurality of teeth within the virtual dentition. For example, virtual articulation module 24 may determine an orthodontic treatment plan (e.g., orthodontic appliances, such as braces or retainers) to correct the orientation of one or more teeth of the maxillary and/or mandibular arch. In some examples, the orthodontic treatment plan may indicate the final, correct orientation for one or more teeth and intermediate orientations of the respective teeth to arrive at the correct orientation. In one example, the treatment plan may include a virtual model of one or more of the dental arches (e.g., to create dentures or dental implants).

While the examples of FIGS. 11 and 12 are described with reference to the tangent vectors associated with left and right lateral excursions to determine proper tooth orientation (e.g., proper or correct torque angle), in some examples, virtual articulation module 24 may utilize tangent vectors associated with protrusive mandibular motions along the anterior guidance to determine whether the posterior teeth are oriented or shaped correctly (e.g., assuming proper anterior guidance). As another example, virtual articulation module 24 may utilize tangent vectors to determine whether the shape and/or orientation of the canines or incisors is correct (or to determine which shape/orientation is correct). For example, virtual articulation module 24 may determine that a canine is oriented correctly in response to determining that a guidance tangent vector (left for left canines, right for right canines) is orthogonal to distal-buccal area in lower canine and orthogonal to mesial-palatine area in upper canine. Further, virtual articulation module 24 may determine that the torque angle of a lower canine is correct based on the open and/or closed tangent vectors. Furthermore, the shapes of the canines or incisors can be modified to achieve proper guidance, and thus protection of the posterior teeth to reduce or eliminate interference between teeth.

In this way, techniques of this disclosure may enable a computing system to determine whether the current orientation and/or shape of one or more of a patient's teeth is correct. Additionally, or alternatively, the computing system may determine the correct orientation and/or shape of the patient's teeth and output information (e.g., to a dental treatment provider) to enable a dental treatment provider to develop a treatment plan. In some examples, the computing system determines the proper torque and tip angles for bicuspids and molars, aspects of proper canine relationship, and aspects of proper incisor relationship (e.g., including proclination angles).

In some examples, a computing device automatically determines the orientations and/or shapes of the teeth based on such analyses and makes the necessary modifications to the dentition without outputting a GUI or receiving user input. The computing device may output the data indicative of the correct shape and/or orientation of the dental anatomy to other systems for further analysis and adjustment of the dentition, or to digital design modules that design, automatically or with user input, devices such as 3D printed models for clear tray aligner formation, 3D printed aligner design, custom bracket design, custom archwire design, dental restoration mold design (for additive methods), custom abrasive tool design (for subtractive methods), or the like. The computing device may output graphical or human-readable instructions or indications for tooth movement or tooth modification. The computing device may output partial guidance for tooth movement or tooth anatomy modification constraints that are used by other systems to further optimize tooth positions or shapes. These outputs might take the form of positional and/or orientation ranges, or definite values for certain point or vector components that constrain one or more axes. In some instances, the output may include data indicating a relative change in tooth surface position, such as an amount of material to add or subtract, or the thickness of a coating, or a radius of curvature of a surface or cusp or fossa, along with the boundary of the modified region.

Figure 13A:
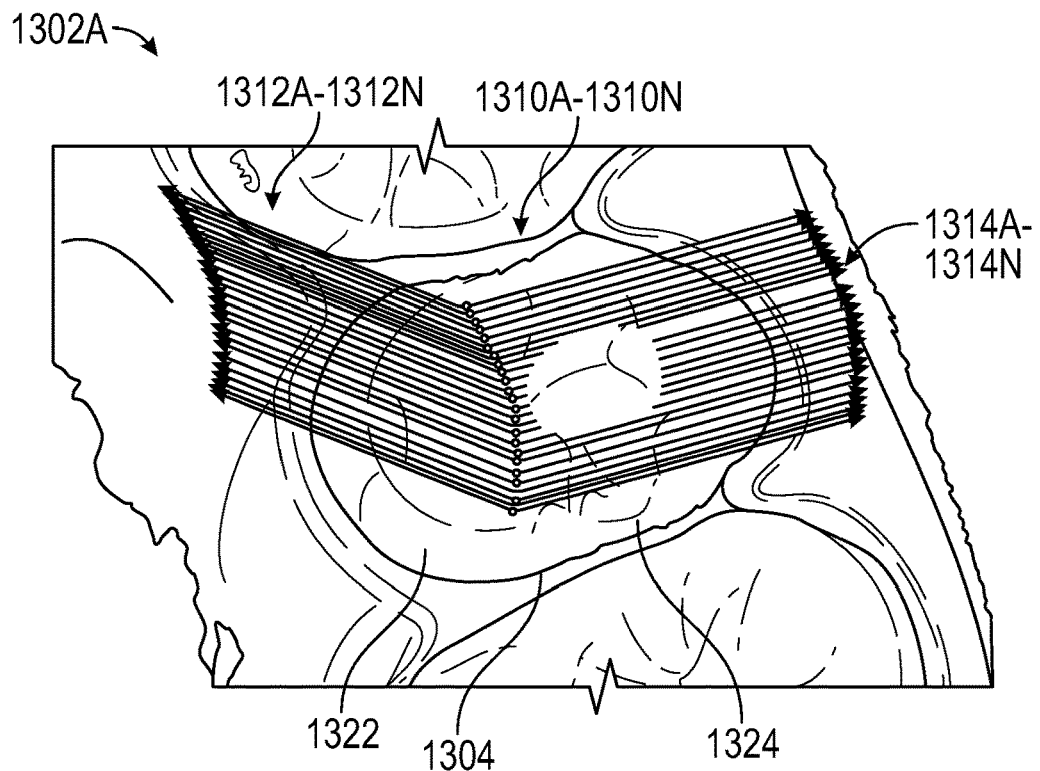
FIGS. 13A-13B illustrate example user interfaces of a portion of a dental arch and a plurality of tangent vectors or rays, according to one example of the disclosure.
Figure 13B:
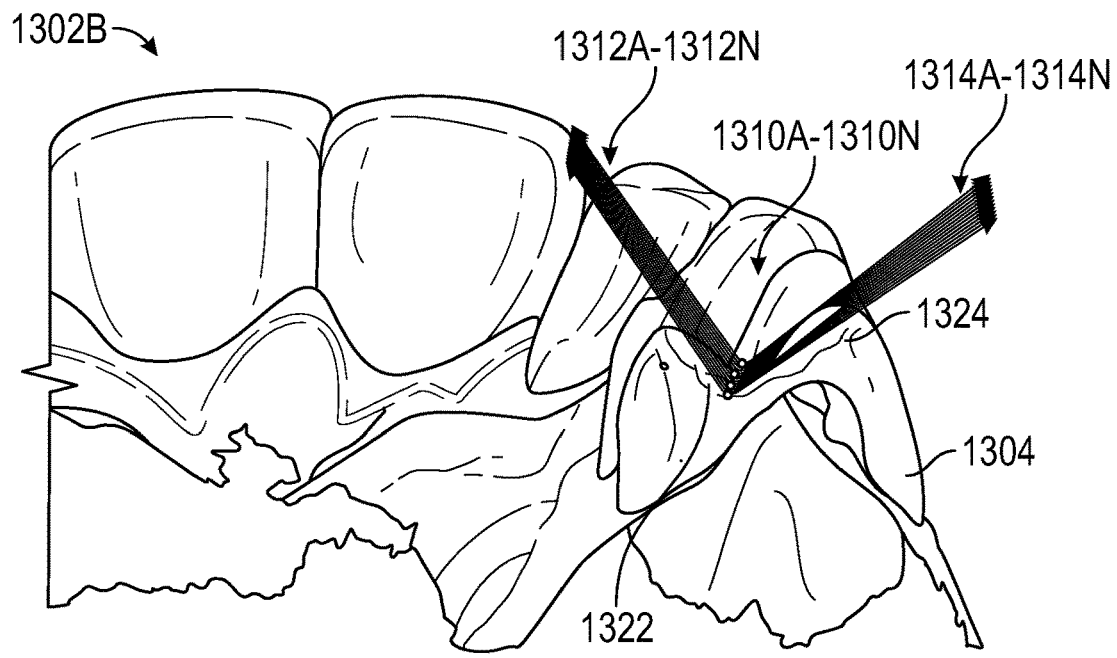

FIG. 13A illustrates an example user interface 1302A according to one example of the disclosure. FIG. 13B illustrates an example user interface 1302B according to one example of the disclosure. FIGS. 13A-13B (collectively, FIG. 13) are described with reference to system 12 of FIG. 1. GUIs 1302A and 1302B (collectively, GUIs 1300) illustrate atop view and a side view of tooth 1304, respectively.

As illustrated in FIG. 13, GUIs 1302 each include graphical representations of a plurality of points 1310A-1310N (collectively, points 1310) within the fossa of tooth 1304. As illustrated in FIG. 13, GUIs 1302 include graphical representations of tangent vectors 1312A-1312N (collectively, tangent vectors 1312) and tangent vectors 1314A-1314N (collectively, tangent vectors 1314) associated with point 1310. Together, tangent vectors 1314 and their respective base points 1310 define rays that have definite positions and directions in the space of the virtual dental anatomy. In the example of FIG. 13, tangent vectors 1312 are associated with a right lateral excursion and tangent vectors 1314 are associated with a left lateral excursion.

Virtual articulation module 24 may determine whether the orientation and/or shape of tooth 1304 is correct based at least in part on one or more of tangent vectors 1312 and/or 1314, as described above with reference to FIGS. 11 and/or FIG. 12. For example, virtual articulation module 24 may determine that the orientation of tooth 1304 is correct in response to determining that the rays defined by tangent vectors 1312 and/or 1314, along with respective base points 1310, do not intersect the surface of lingual cusp 1322 or the surface of buccal cusp 1324. In one instance, virtual articulation module 24 determines that the orientation of tooth 1304 is not correct in response to determining that one or more of the rays defined by tangent vectors 1314 and respective base points 1310 intersect the surface of buccal cusp 1324.

Figure 14:
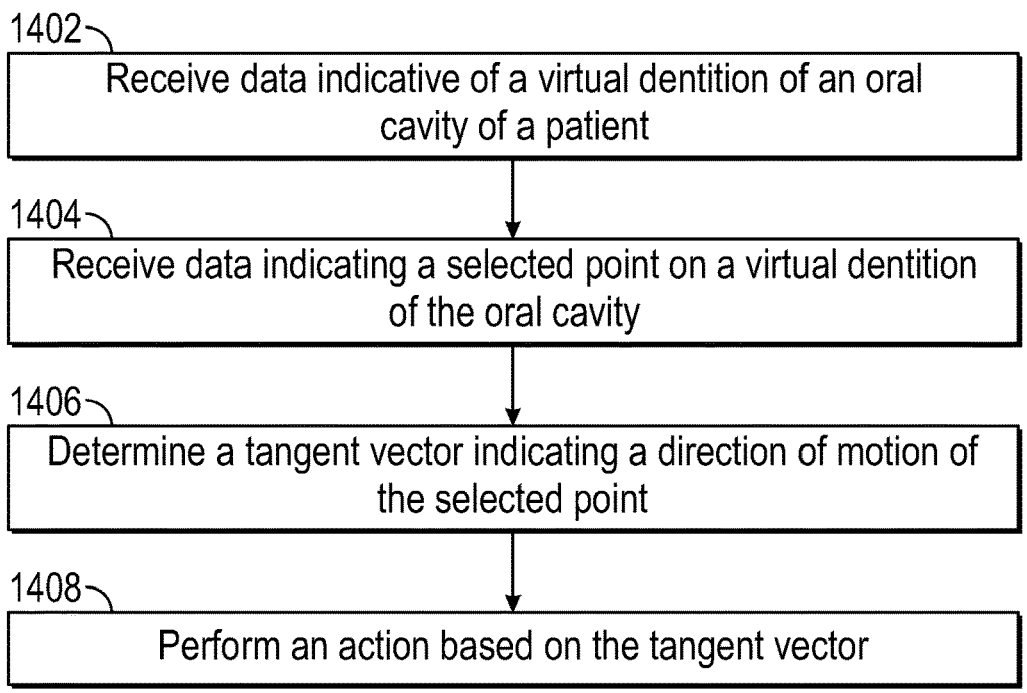
FIG. 14 is a flow diagram showing one example process using the techniques of the disclosure.

FIG. 14 is a flow diagram showing one example process using the techniques of the disclosure. FIG. 14 is described with reference to the system described in FIG. 1.

Computing system 14 may receive data indicative of a virtual dentition of an oral cavity of a patient (1402). For example, the data indicative of the virtual dentition may include data indicative of a virtual mandibular arch representing a mandibular arch of the patient or a virtual maxillary arch representing a maxillary arch of the patient. In some examples, computing system 14 receives data indicative of the virtual dentition directly in vivo using an intraoral scanner, Cone Beam Computed Tomography (CBCT) scanning (i.e., 3D X-ray), or Magnetic Resonance Imaging (MRI). In other examples, computing system 14 may receive data indicative of the dentition indirectly by scanning an impression of the teeth or a casting made from an impression of the teeth. In yet another example, computing system 14 may receive data indicative of the patient's dentition from another computing device, for example, over a network.

In some examples, computing system 14 receives data indicating a selected point of the virtual dentition of the patient's oral cavity (1404). For example, computing system 14 may output a graphical user interface (GUI) that includes a graphical representation of at least a portion of the patient's oral cavity, such as an image of the virtual mandibular arch and/or virtual maxillary arch. Computing system 14 may receive data indicative of a user input (e.g., via input device 18) selecting one or more points within the patient's oral cavity. As another example, computing system 14 may select one or more points on the dentition. For example, computing system 14 may select one or more points in the fossa of one or more teeth or one or more points on a surface (e.g., within a wear facet) of one or more teeth.

In some examples, computing system 14 determines one or more tangent vectors for the selected point (1406). In some examples, each of the tangent vectors is tangent to a circular arc centered on the respective rotational axis and indicates a direction of motion of the selected point. In some examples, computing system 14 determines rays defined by the one or more tangent vectors and the selected point (1406).

Computing system 14 performs one or more actions in response to determining the tangent vector (1408). In one example, computing system 14 performs an action by outputting a GUI 30 indicative of the dentition and tangent vector to display device 16. Computing system 14 may, in some examples, perform an action by determining whether a particular tooth is oriented and/or shaped correctly. In yet another example, computing system 14 may perform an action by determining whether the particular tooth is oriented correctly for axial loading of the particular tooth.

In some scenarios, computing system 14 performs an action by updating or modifying the virtual dentition, for example, by updating an orientation and/or shape of one or more teeth. In another scenario, computing system 14 performs an action by determining one or more treatment plans for the patient's teeth.

Figure 15:
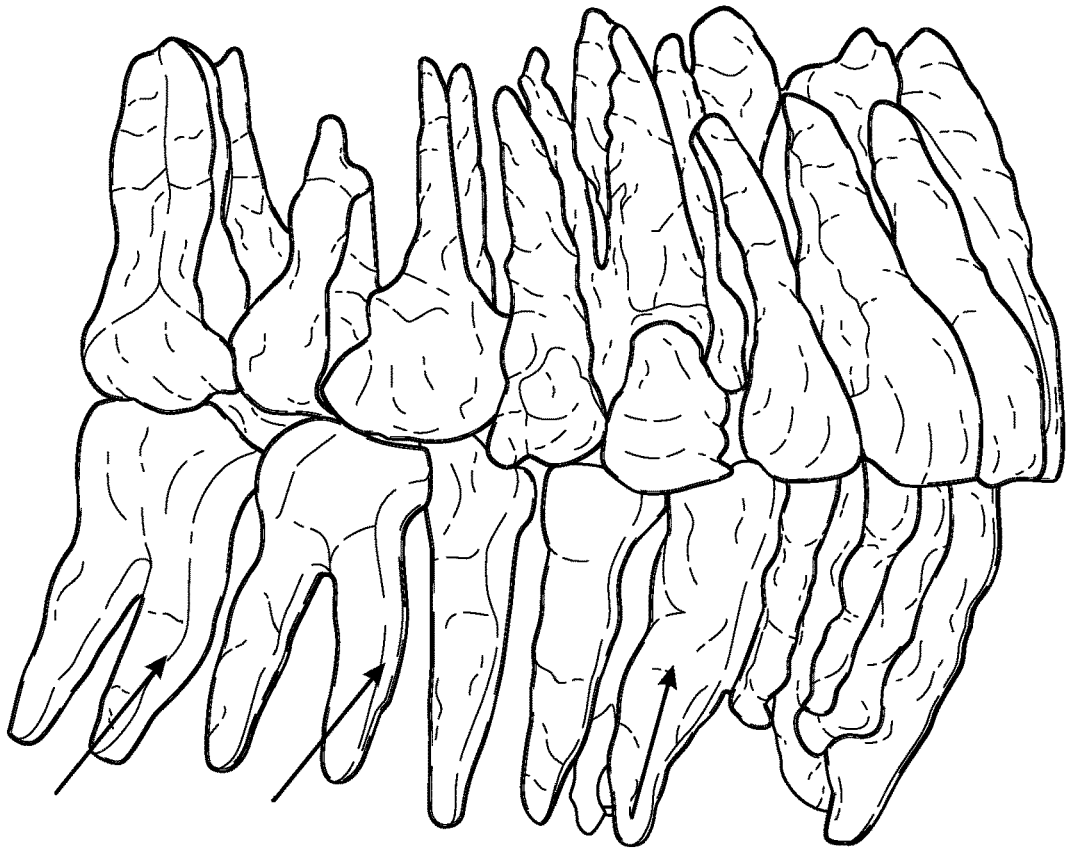
FIG. 15 illustrates an example 3D digital model of dental arches including roots, according to one example of the disclosure.

FIG. 15 illustrates an example 3D digital model of dental arches including roots, according to one example of the disclosure. FIG. 15 is described with reference to system 10 of FIG. 1. Virtual articulation module 24 may determine a plurality of tangent vectors 1502A-1502C (collectively, tangent vectors 1502) associated with different roots of the dental anatomy. Tangent vectors 1502 may indicate an initial direction of the roots for an open gape excursion. Computing system 14 may determine that a given tooth is not oriented correctly in response to determining that the root for the given tooth is not parallel to the respective tangent vector 1502. In such examples, computing system 14 may rotate the tooth until the root is parallel to the tangent vector 1502.

Figure 16A:
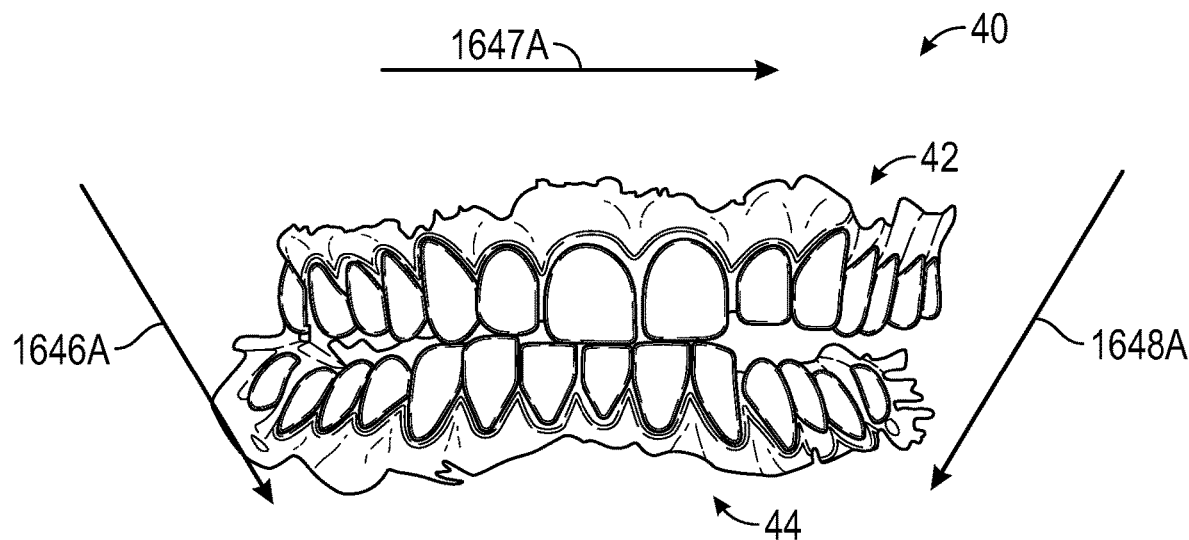
FIGS. 16A-16C illustrate a digital 3D model of dental arches, according to one example of the disclosure.
Figure 16B:
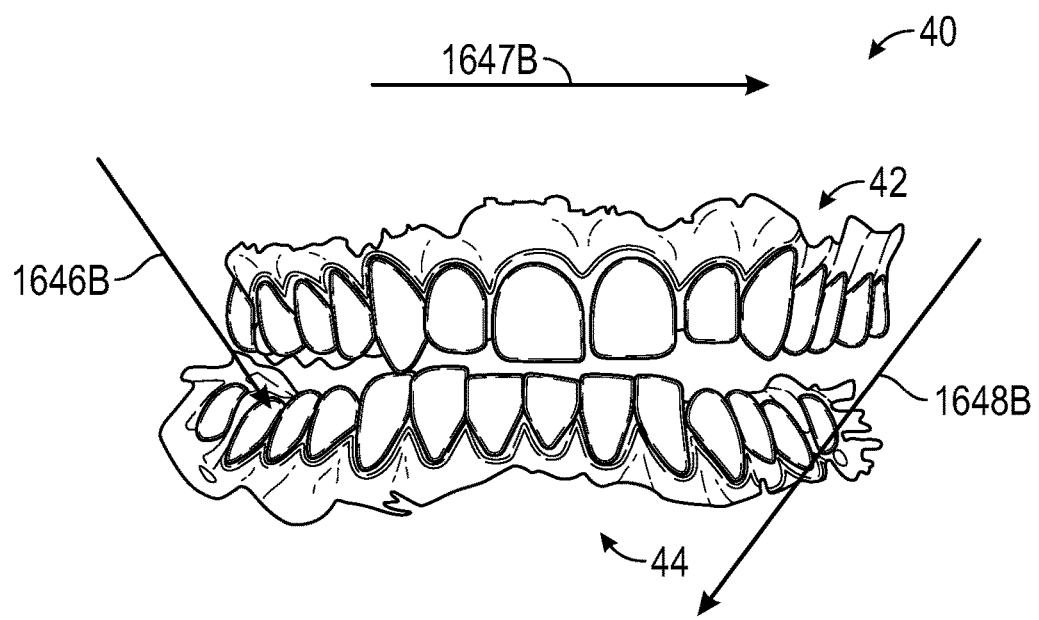

FIGS. 16A-16B illustrate a digital 3D model of dental arches, according to one example of the disclosure. FIG. 16 are described with reference to system 10 of FIG. 1.

Digital 3D model 40 includes virtual maxillary arch 42 and virtual mandibular arch 44. FIG. 16A illustrates example rotational axes 1646A, 1647A, and 1648A prior to modifying the guidance canines. FIG. 16B illustrates example rotational axes 1646B, 1647B, and 1648B after modifying the guidance canines (e.g., by increasing the height of the canines).

In the example of FIG. 16, rotational axes 1646A and 1646B indicate the right guidance of virtual mandibular arch 44, rotational axes 1647A and 1647B indicate the open gape of virtual mandibular arch 44, and rotational axes 1648A and 1648B indicate the left guidance of virtual mandibular arch 44.

Figure 16C:
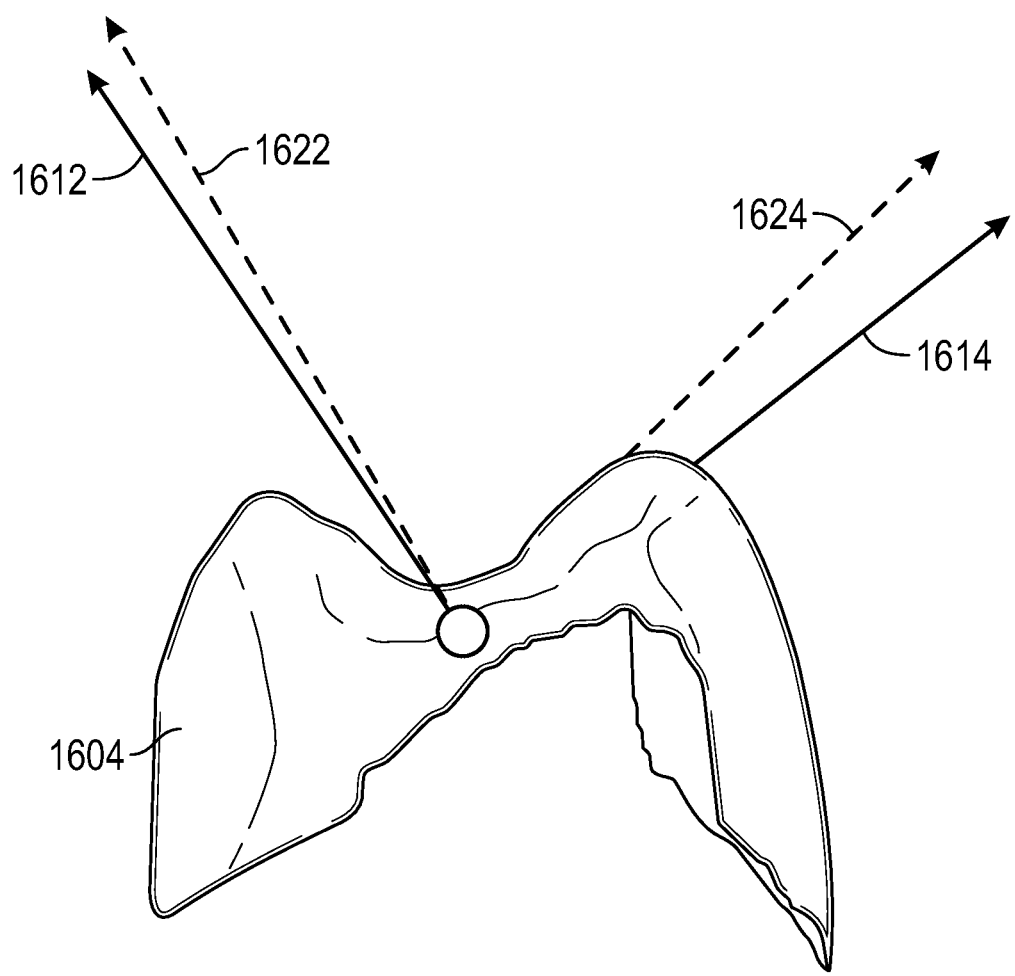

FIG. 16C illustrates the effect of modifying the shape of the guidance canines based on the tangent vectors for point 1610 of tooth 1604. Tangent vector 1612 illustrates the initial motion of point 1610 for a right lateral excursion and tangent vector 1614 illustrates the initial motion of point 1610 for a left lateral excursion prior to modifying the guidance canines. Tangent vector 1622 illustrates the initial motion of point 1610 for a right lateral excursion and tangent vector 1624 illustrates the initial motion of point 1610 for a left lateral excursion after modifying the guidance canines. As illustrated in FIG. 16C, the angle between tangent vectors 1622 and 1624 is less than the angle between tangent vectors 1612 and 1614, which provides additional tolerance to adjust the torque/orientation of tooth 1604.

Figure 17:
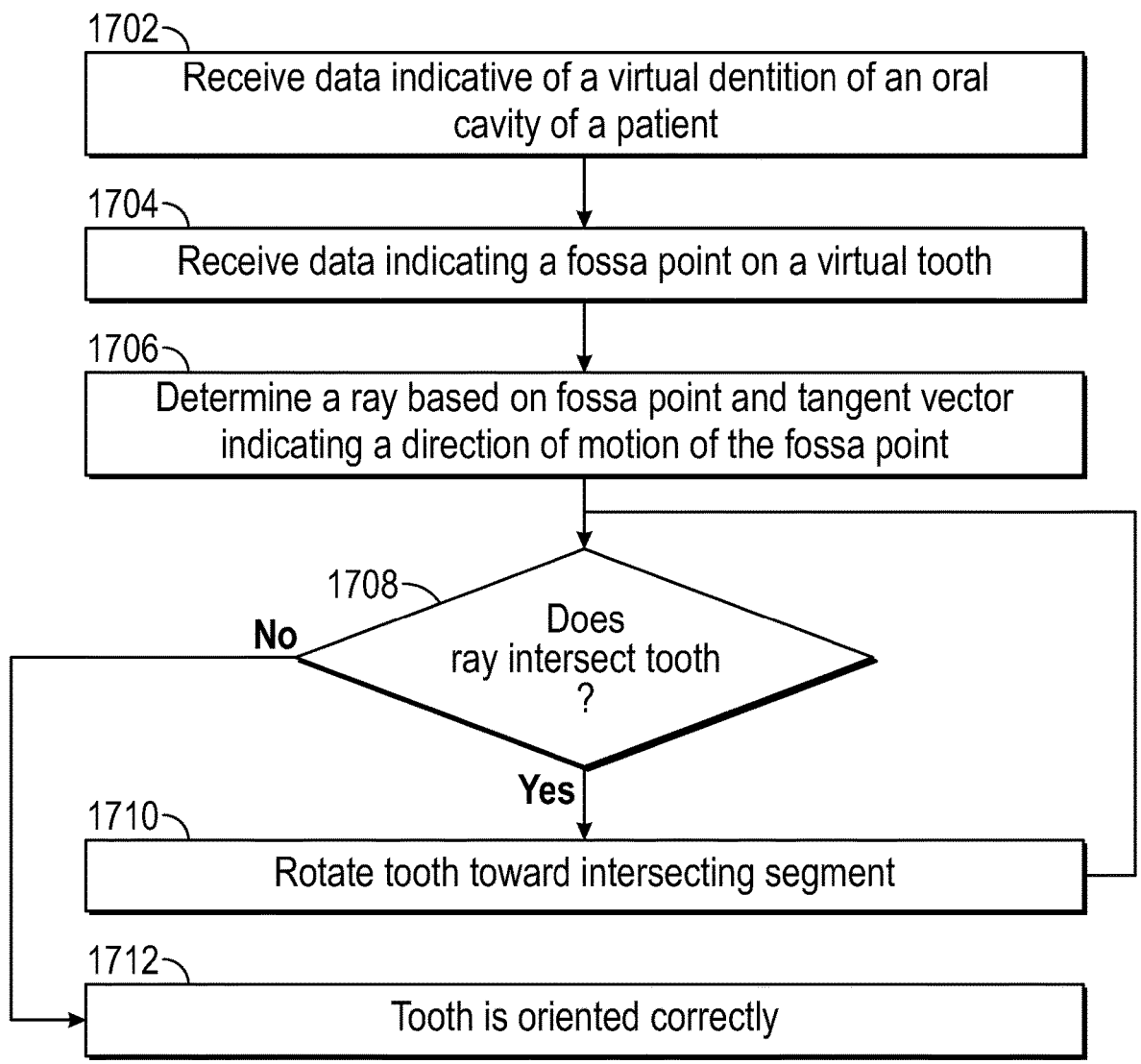
FIG. 17 is a flow diagram showing one example process using the techniques of the disclosure.

FIG. 17 is a flow diagram showing one example process using the techniques of the disclosure. FIG. 17 is described with reference to system 10 of FIG. 1. In the example of FIG. 17, computing system 14 of FIG. 1 may determine whether a tooth is oriented correctly based at least in part on one or more tangent vectors.

Computing system 14 receives data indicative of a virtual dentition of an oral cavity of a patient (1702). In one example, the virtual dentition includes a single-cusp tooth (e.g., an incisor, a cuspid, or a bicuspid with a degenerate lingual cusp) or a multi-cusp tooth (e.g., a bicuspid or molar).

In some examples, computing system 14 receives data indicating a fossa point on a virtual tooth (e.g., molar or bicuspid tooth) of the virtual dentition (1704). For example, computing system 14 may receive a user input selecting the point in the fossa of the tooth. In another example, computing system 14 selects the point in the fossa.

Computing system 14 determines a ray based on a fossa point and a tangent vector indicating motion of the fossa point (1706). The tangent vector indicates a particular direction of motion of the selected fossa point.

In some examples, computing system 14 determines whether the ray defined by the tangent vector and the fossa point intersects a surface of the tooth (1708). For example, computing device 15 may determine whether or where the ray intersects a crown of a virtual tooth. Computing system 14 may determine a magnitude of the intersection by determining a distance between an intersection point where the ray enters the tooth and an intersection point where the ray exits the tooth.

Computing system 14 rotates the tooth towards the point of intersection (1710) in response to determining that the ray intersects a surface of the tooth ("YES" branch of 1708). Computing system 14 may rotate the tooth in fixed angular increments or variable angular increments. For example, computing system 14 may rotate the tooth in relatively small fixed increments (e.g., 1-degree).

Responsive to determining that the ray does not intersect a surface of the tooth ("NO" branch of 1708), computing system 14 may determine that the tooth is oriented correctly (1710). In such examples, computing system 14 may stop rotating the tooth in response to determining that the tooth is oriented correctly.

In some instances, computing system 14 rotates the tooth in variable increments. For instance, computing system 14 may perform a first rotation by rotating the tooth by a relatively large angle and perform subsequent rotations by rotating the tooth in decreasing increments (e.g., half the angle of the previous rotation). In such instances, computing system 14 may change the direction of the rotation in response to determining that the ray defined by the tangent vector and the fossa point does not intersect the surface of the tooth. Computing system 14 may stop rotating the tooth when the size of the rotation increment satisfies (e.g., is less than or equal to) a threshold size. In such examples, computing system 14 may converge on an optimal torque angle for the tooth more quickly and/or more accurately than rotating the tooth in fixed increments.

Figure 18:
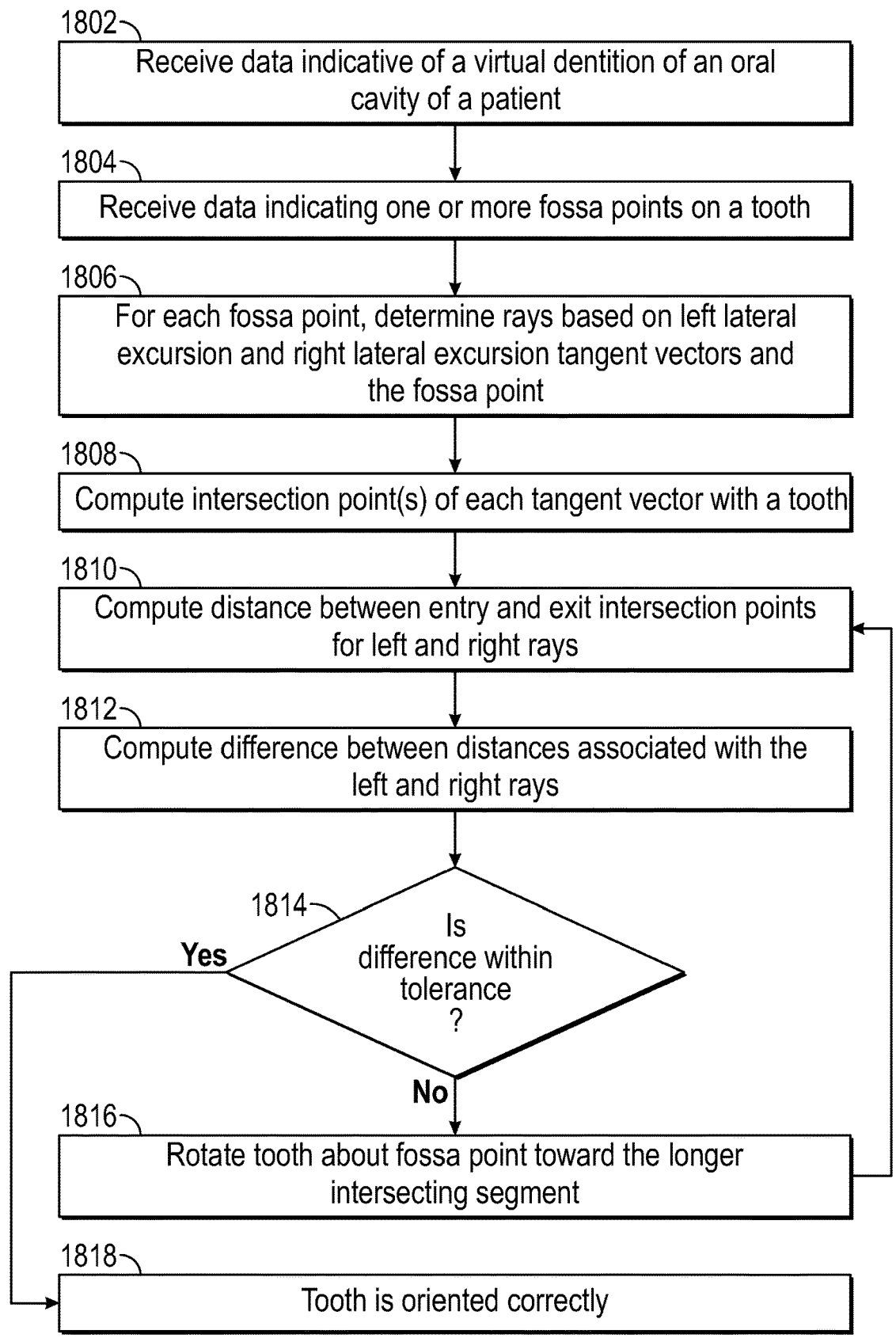
FIG. 18 is a flow diagram showing one example process using the techniques of the disclosure.

FIG. 18 is a flow diagram showing one example process using the techniques of the disclosure. FIG. 18 is described with reference to system 10 of FIG. 1. In the example of FIG. 18, computing system 14 of FIG. 1 may determine whether a tooth is oriented correctly based at least in part on one or more tangent vectors.

Computing system 14 receives data indicative of a virtual dentition of an oral cavity of a patient (1802). In some examples, computing system 14 receives data indicating one or more fossa points on a virtual tooth (e.g., molar or bicuspid tooth) of the virtual dentition (1804). For example, computing system 14 may receive a user input selecting the points in the fossa of the tooth. In another example, computing system 14 selects the points in the fossa.

Computing system 14 determines rays based on a left lateral excursion tangent vector and a right lateral excursion tangent vector for each fossa point (1806). The tangent vector indicates a particular direction of motion of the respective fossa point.

In some examples, computing system 14 computes intersection points (if any) for each ray defined by tangent vector (1808) and its respective fossa point. For example, computing system 14 determines intersection points between one of the rays defined in part by the lateral excursion tangent vectors and a buccal cusp of a tooth (e.g., a molar or bicuspid) and intersection points between rays defined in part by the other lateral excursion tangent vectors and the lingual cusp of the tooth. Additionally, or alternatively, computing system 14 may determine intersection points (if any) between the rays defined in part by the protrusive or retrusive excursion tangent vectors and the mesial or distal cusps of the same tooth.

In the example of FIG. 18, for each tangent vector that intersects the surface of the tooth, computing system 14 may compute a distance between an entry intersection point (e.g., a point where the ray enters the tooth) and an exit intersection point (e.g., a point where the ray exits the tooth) (1810). A line segment between the entry intersection point and the exit intersection point is referred to as an intersecting segment. For example, computing system 14 may determine a distance of an intersecting segment associated with the left lateral excursion tangent vector by computing a distance between the entry and exit intersection points for the ray defined in part by the left lateral excursion tangent vector. Similarly, computing system 14 may determine a distance of an intersecting segment associated with the right lateral excursion tangent vector by computing a distance between the entry and exit intersection points for the ray defined in part by the right lateral excursion tangent vector.

In examples where multiple tangent vectors intersect a single cusp of the tooth, computing system 14 may determine a summary distance of the intersecting segments associated with the respective left lateral excursion tangent vectors and a summary distance of the intersecting segments associated with the respective right lateral excursion tangent vectors. Computing system 14 may determine the summary distances by computing a maximum distance between entry and exits points, an average distance between entry and exit point, or a combined (e.g., sum) distance between entry and exit points for the rays that intersect a given cusp. In other words, in computing system 14 the summary distance associated with the left lateral excursion tangent vectors is a max, average, or sum of the distances of the intersecting segments for the left lateral excursion tangent vectors, and the summary distance associated with the right lateral excursion tangent vectors is a max, average, or sum of the distances of the intersecting segments for the right lateral excursion tangent vectors.

Computing system 14 may determine a difference between the distances associated with the right ray (e.g., associated with the right lateral excursion tangent vector(s)) and the distances associated with the left ray (e.g., associated with the left lateral excursion tangent vector(s)) (1812). For example, computing system 14 may determine a difference in the distance of the intersecting segments for the left lateral excursion tangent vector and the distance of the intersecting segments for the right lateral excursion tangent vector. In other words, computing system 14 subtracts the distance of the intersecting segment associated with the left lateral excursion tangent vector from the distance of the intersecting segment associated with the right lateral excursion tangent vector (or vice versa). In examples with multiple left and right lateral excursion tangent vectors, computing system 14 determines a difference between the summary distance of the intersecting segment associated with the left lateral excursion tangent vectors and the summary distance of the intersecting segment associated with the right lateral excursion tangent vectors.

In some examples, computing system 14 determines whether the difference is within a tolerance (1814). When the difference between the distance of the intersecting segment associated with the left lateral excursion vector and the distance of the intersecting segment associated with the right lateral excursion vectors is within the tolerance or threshold, this may indicate that the cusps of the tooth are approximately centered between the tangent vectors for the selected points. Thus, computing system 14 may determine that the tooth is oriented correctly (1818) in response to determining that the difference between the distance associated with the left lateral excursion vector and the distance associated with the right lateral excursion vectors is within the tolerance or threshold ("YES" branch of 1814).

Computing system 14 rotates the tooth (1816) in response to determining that the difference is not within the tolerance ("NO" branch of 1814). Computing system 14 may rotate the tooth about the fossa towards the longer of intersecting segment associated with the left lateral excursion vector and the intersecting segment associated with the right lateral excursion vectors. In other words, if the intersecting segment associated with the left lateral excursion tangent vector is longer than the intersecting segment associated with the right lateral excursion tangent vector, then computing system 14 rotates the tooth towards the cusp associated with the left lateral excursion tangent vector. Said yet another way, if the left lateral excursion tangent vector intersects more of the tooth than the right lateral excursion tangent vector, computing system 14 rotates the tooth towards the cusp associated with the left lateral excursion tangent vector. Similarly, computing system 14 may rotate the tooth about a bucco-lingual axis passing through the fossa point, rather than about a mesio-distal axis passing through the fossa point. In this way, computing system 14 may balance or center the orientation of the dental anatomy with respect to the tangent vectors.

Computing system 14 may rotate the tooth in fixed angular increments or variable angular increments. For example, computing system 14 may rotate the tooth in relatively small fixed increments (e.g., 1-degree). In some instances, computing system 14 rotates the tooth in variable increments. For instance, computing system 14 may perform a first rotation by rotating the tooth by relatively large angle and perform subsequent rotations by rotating the tooth in decreasing increments (e.g., half the angle of the previous rotation). In such instances, computing system 14 may change the direction of the rotation in response to determining the tooth has been over-rotated. For example, computing system 14 may determine the tooth has been over-rated in response to determining the difference between the distances associated with the right lateral excursion tangent vector(s) and the distances associated with the left lateral excursion tangent vector(s) has changed signs (e.g., the difference has gone from positive to negative or negative to positive).

In some cases, computing system 14 may not completely remove the intersection of the tangent vector and the tooth (e.g., because at least a portion of dental anatomy will remain in the path of a tangent vector). In such examples, computing system 14 may also correct the dental anatomy by other means, such as by increasing the length of the appropriate one or both canines to increase the slope of the gape angle as a function of lateral excursion angle.

Figure 19:
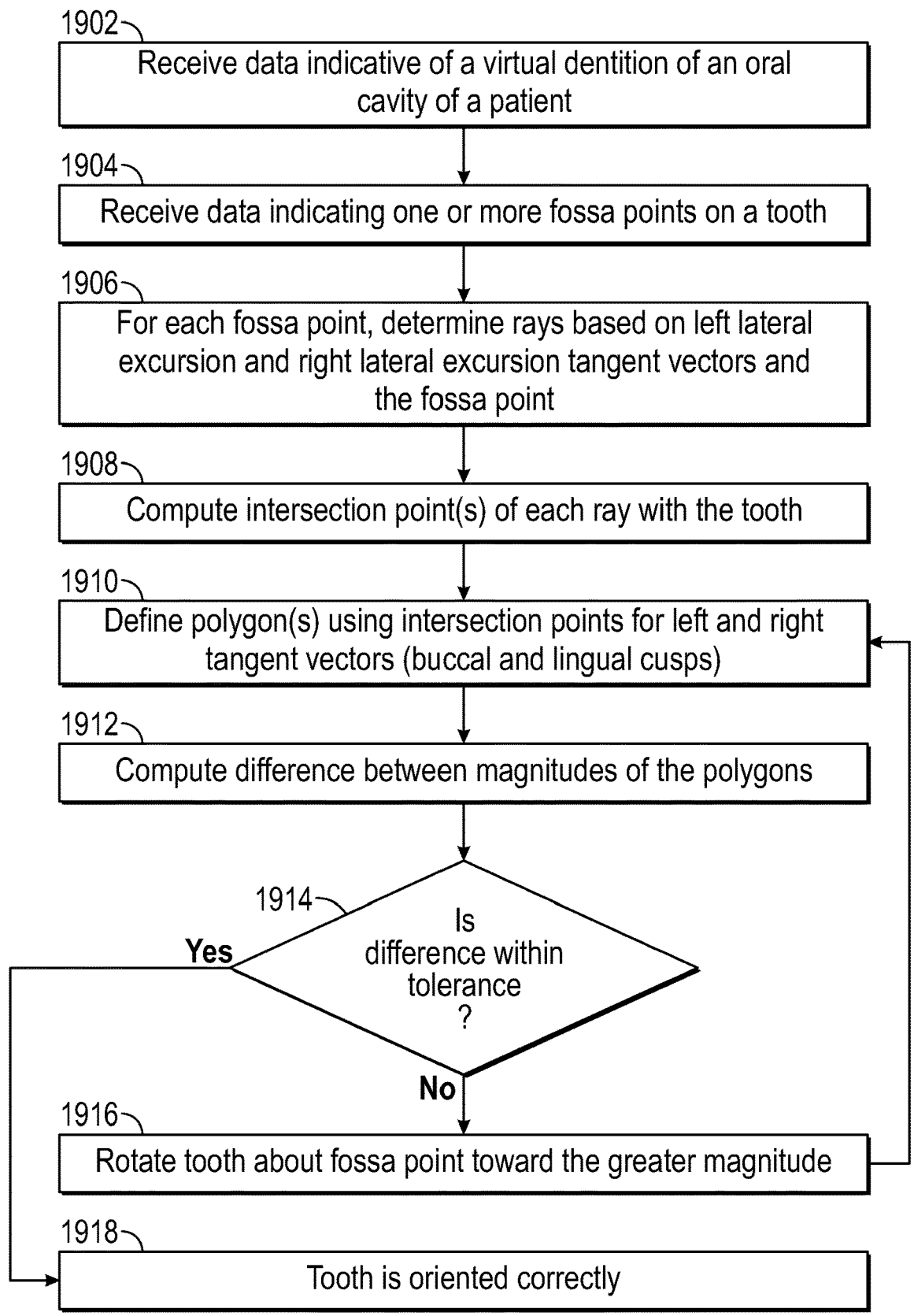
FIG. 19 is a flow diagram showing one example process using the techniques of the disclosure.

FIG. 19 is a flow diagram showing one example process using the techniques of the disclosure. FIG. 19 is described with reference to system 10 of FIG. 1. In the example of FIG. 19, computing system 14 of FIG. 1 may determine whether a tooth is oriented correctly based at least in part on one or more tangent vectors.

Computing system 14 receives data indicative of a virtual dentition of an oral cavity of a patient (1902). In some examples, computing system 14 receives data indicating one or more fossa point on a virtual tooth (e.g., molar or bicuspid tooth) of the virtual dentition (1904). For example, computing system 14 may receive a user input selecting the points in the fossa of the tooth. In another example, computing system 14 selects the points in the fossa.

Computing system 14 determines rays based on a left lateral excursion tangent vector, a right lateral excursion tangent vector, and the fossa point (1906). The tangent vector indicates a particular direction of motion of the selected point.

In some examples, computing system 14 computes intersection points (if any) of each ray with a tooth (1908). For example, computing system 14 determines intersection points between one of the rays defined in part by lateral excursion tangent vectors and a buccal cusp of a tooth (e.g., a molar or bicuspid) and intersection points between the ray defined in part by the other lateral excursion tangent vector and the lingual cusp of the tooth. Additionally, or alternatively, computing system 14 may determine intersection points (if any) between the rays defined in part by the protrusive or retrusive excursion tangent vectors and the mesial or distal cusps of the same tooth.

In the example of FIG. 19, computing system 14 may define a polygon based on the intersection points of the respective ray that intersect the surface of the tooth. For example, computing system 14 may compute a first polygon associated with the left lateral excursion tangent vectors whose respective rays intersect the tooth and a second polygon associated with the right lateral excursion tangent vectors whose respective rays intersect the tooth. In other words, the rays form a kind of non-planar sheet that may intersect a portion of the dental anatomy. The boundary of intersection may be defined discretely as a polygon comprising a finite number of points where a respective finite number of rays intersect a portion of the dental anatomy (where the associated rays enter and exit the anatomy).

Computing system 14 determines a magnitude of each of the polygons. In some examples, computing system 14 determines the magnitude by computing the perimeter length of the polygon. As another example, computing system 14 may compute the magnitude by projecting the 3D polygon onto a plane and determining the area that the projected 3D polygon encloses or summing the polygonal areas defined by adjacent line segments where respective rays enter and exit the dental anatomy. In another other example, computing system 14 may determine the magnitude by computing a volume of a space defined on one side by the polygonal area on the sheet of rays intersecting the dental anatomy and on the other side by the surface of the dental anatomy penetrating the sheet. In yet another example, computing system 14 may determine the magnitude by computing the maximum distance between any point on the penetrated dental anatomy and a respective point on the sheet of rays as projected perpendicular to the sheet of rays. In this way, computing system 14 determines a magnitude of the first polygon associated with the left lateral excursion tangent vectors that intersect the tooth and a magnitude of intersection for the second polygon associated with the right lateral excursion tangent vectors.

Computing system 14 determines the difference between the magnitude of the first polygon and the magnitude of the second polygon (1912).

Computing system 14 determines whether the difference in the magnitudes of the polygons is within a tolerance or threshold (1914). When the difference in the magnitudes of the polygons is within the tolerance, this may indicate that the cusps of the tooth are approximately centered between the tangent vectors for the selected points. Thus, computing system 14 may determine that the tooth is oriented correctly (1918) in response to determining that the difference between the distance associated with the left lateral excursion vector and the distance associated with the right lateral excursion vectors is within the tolerance or threshold ("YES" branch of 1914).

Computing system 14 rotates the tooth (1916) in response to determining that the difference is not within the tolerance ("NO" branch of 1914). Computing system 14 may rotate the tooth about the fossa towards the larger polygon (e.g., the polygon having the greater magnitude) (1916). In other words, if the polygon defined by the left lateral excursion tangent vectors is greater than the polygon defined by the right lateral excursion tangent vectors, then computing system 14 rotates the tooth towards the cusp associated with the left lateral excursion tangent vectors. Similarly, computing system 14 may rotate the tooth about a bucco-lingual axis passing through the fossa point, rather than about a mesio-distal axis passing through the fossa point. In this way, computing system 14 may balance or center the orientation of the dental anatomy with respect to the tangent vectors.

Computing system 14 may rotate the tooth in fixed angular increments or variable angular increments. For example, computing system 14 may rotate the tooth in relatively small fixed increments (e.g., 1-degree). In some instances, computing system 14 rotates the tooth in variable increments. For instance, computing system 14 may perform a first rotation by rotating the tooth by a relatively large angle and perform subsequent rotations by rotating the tooth in decreasing increments (e.g., half the angle of the previous rotation). In such instances, computing system 14 may change the direction of the rotation in response to determining the tooth has been over-rotated. For example, computing system 14 may determine the tooth has been over-rated in response to determining the difference between the magnitude of the polygon associated with the right lateral excursion tangent vector(s) and the magnitude of the polygon associated with the left lateral excursion tangent vector(s) has changed signs (e.g., the difference has gone from positive to negative or negative to positive).

In some cases, computing system 14 may not completely remove the intersection of the tangent vector and the tooth (e.g., because at least a portion of dental anatomy will remain in the path of a tangent vector). In such examples, computing system 14 may also correct the dental anatomy by other means, such as by increasing the length of the appropriate one or both canines to increase the slope of the gape angle as a function of lateral excursion angle.

Figure 20:
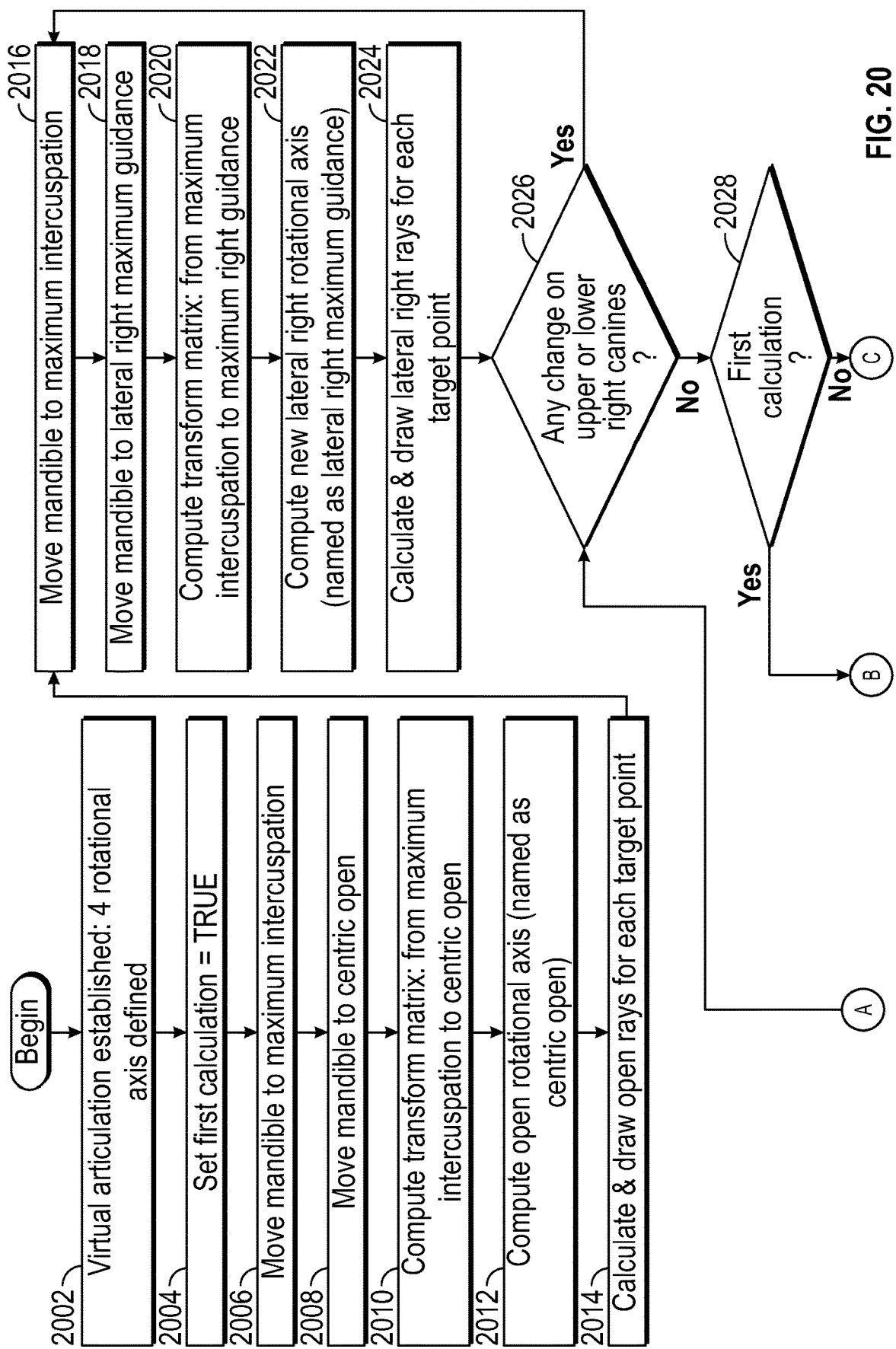
FIG. 20 is a flow diagram showing one example process using the techniques of the disclosure.
Figure 20:
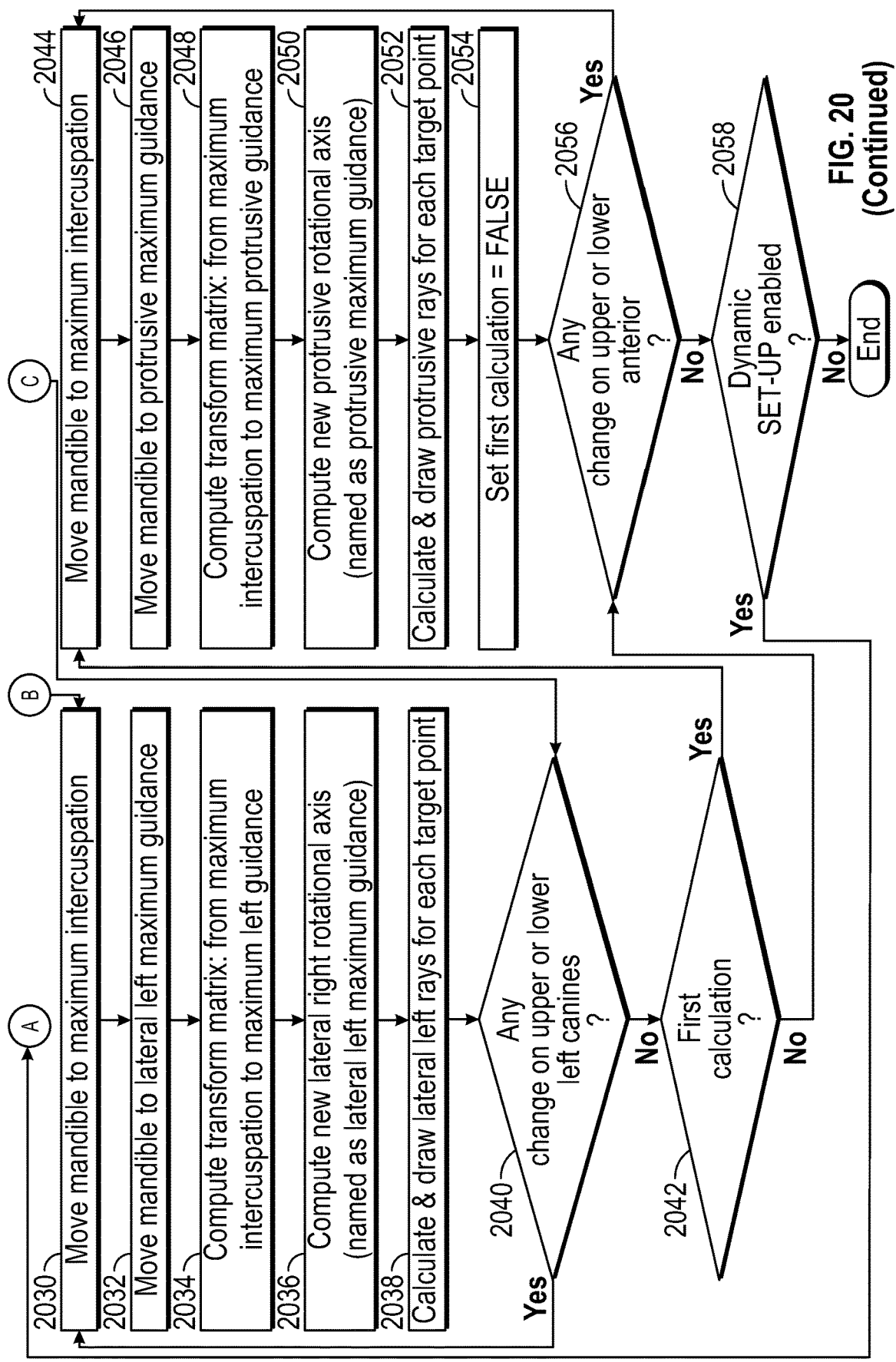

FIG. 20 is a flow diagram showing one example process using the techniques of the disclosure. FIG. 20 is described with reference to system 10 of FIG. 1.

Computing system 14 virtually articulates a 3D model of the patient's dentition to define the four rotational axes associated with movement of the virtual mandibular arch (2002). Computing system 14 sets a flag that indicates whether the current set of calculation is the first set of calculations to true (2004). The first set of calculations refers to the first set of calculations to determine the set of rotational axes. In other words, the flag indicates whether computing system 14 has previously calculated all four rotational axes (e.g., flag=FALSE when the computing system has previously calculated all four rotational axes) or whether computing system 14 has yet to calculate all four rotational axes (e.g., flag=TRUE).

Computing system 14 moves, or virtually articulates the virtual mandibular arch to a maximum intercuspation position (2006). Computing system 14 then moves the virtual mandibular arch to a centric open position (2008). Computing system 14 computes a transform matrix that defines motion of the virtual mandibular arch from the maximum intercuspation position to centric open position (2010). Computing system 14 computes an open rotational axis, which may also be referred to as a centric open rotational axis (2012). Computing system 14 calculates and draws open rays for each target point (2014). In some examples, each open ray indicates a direction of motion of each respective target point for an open excursion.

In one example, computing system 14 moves or virtually articulates the virtual mandibular arch to a maximum intercuspation position (2016). Computing system 14 then moves the virtual mandibular arch to a right maximum guidance position (2018). Computing system 14 computes a transform matrix that defines motion of the virtual mandibular arch from the maximum intercuspation position to the right maximum guidance position (2020). Computing system 14 computes a lateral right rotational axis, which may also be referred to as a lateral right maximum guidance rotational axis (2022). Computing system 14 computes and draws lateral right rays for each target point (2024). In some examples, each lateral right ray indicates a direction of motion for each respective target point for a right lateral excursion.

Computing system 14 determines whether there has been any change to the upper or lower right canines (2026). Computing system 14 re-positions the virtual mandibular arch at the maximum intercuspation position (2016) if there has been any change to the right canines ("Yes" branch of 2026). If there has not been any changes to the right canines ("No" branch of 2026), computing system 14 determines whether the current set of calculations is still the first set of calculations (e.g., whether computing system 14 has yet to calculate all four rotational axes, such that the flag=TRUE) (2028). If the current set of calculations is not the first set of calculations ("NO" branch of 2028), computing system 14 determines whether there has been a change to the lower left canines (2040).

In one example, computing system 14 moves or virtually articulates the virtual mandibular arch to the maximum intercuspation position (2030) if the current set of calculations is still the first set of calculations ("YES" branch of 2028). Computing system 14 then moves the virtual mandibular arch to a left maximum guidance position (2032). Computing system 14 computes a transform matrix that defines motion of the maximum intercuspation position to the left maximum guidance position (2034).

Computing system 14 computes a lateral left rotational axis, which may also be referred to as a lateral left maximum guidance rotational axis (2036). Computing system 14 computes and draws lateral left rays for each target point (2038). In some examples, each lateral left ray indicates a direction of motion for each respective target point for a left lateral excursion.

Computing system 14 determines whether there has been any change to the upper or lower left canines (2040). Computing system 14 re-positions the virtual mandibular arch at the maximum intercuspation position (2030) if there has been any change to the left canines ("Yes" branch of 2040). If there has not been any changes to the left canines ("No" branch of 2030), computing system 14 determines whether the current set of calculations is still the first set of calculations (e.g., whether computing system 14 has yet to calculate all four rotational axes, such that the flag=TRUE) (2042). If the current set of calculations is not the first set of calculations ("NO" branch of 2042), computing system 14 determines whether there has been a change to an upper or lower anterior tooth (2056).

In one example, computing system 14 moves or virtually articulates the virtual mandibular arch to the maximum intercuspation position (2044) if the current set of calculations is still the first set of calculations ("YES" branch of 2042). Computing system 14 then moves the virtual mandibular arch to a maximum protrusive guidance position (2046). Computing system 14 computes a transform matrix that defines motion of the virtual mandibular arch from the maximum intercuspation position to the maximum protrusive guidance position (2048). Computing system 14 computes a protrusive rotational axis, which may also be referred to as a protrusive maximum guidance rotational axis (2050). Computing system 14 computes and draws protrusive rays for each target point (2052). In some examples, each protrusive ray indicates a direction of motion for each respective target point for a protrusive excursion.

After calculating the centric open rotational axis, the lateral right rotational axis, the lateral left rotational axis, and the protrusive rotational axis, computing system 14 updates the flag (e.g., by setting the flag to false) to indicate that the all four rotational axes have been calculated (2054).

Computing system 14 determines whether there has been any change to the upper or lower anterior teeth (2056). Computing system 14 re-positions the virtual mandibular arch at the maximum intercuspation position (2044) if there has been any change to the anterior teeth ("Yes" branch of 2056).

If there has not been any changes to the anterior teeth ("No" branch of 2056), computing system 14 determines whether a dynamic setup is enabled (2058). Computing system 14 re-determines whether there has been any changes to the teeth (2026) if the dynamic setup has been enabled ("YES" branch of 2058). Computing system 14 ends the process if the dynamic setup has not been enabled ("NO" branch of 2058).

Various examples have been described. These and other examples are within the scope of the following claims.

What is claimed is:

1. A method comprising:
receiving, by a computing device, data indicative of a virtual dentition of an oral cavity of a patient, the data indicative of the virtual dentition including data indicative of at least one of a virtual mandibular arch representing a mandibular arch of the patient or a virtual maxillary arch representing a maxillary arch of the patient;
receiving, by the computing device, data indicating a selected point on the virtual dentition of the oral cavity;
determining, by the computing device, based on a rotational axis of the virtual mandibular arch, a tangent vector indicating a direction of motion of the selected point, wherein the rotational axis defines a center of a circular arc, the circular arc defining a plane that is perpendicular to the rotational axis; and
performing, by the computing device, an action based on the tangent vector.

2. The method of claim 1, wherein performing the action comprises determining, by the computing device, based on the tangent vector, whether an orientation of a tooth of the virtual dentition or a shape of the tooth is correct.

3. The method of claim 2, wherein determining whether the orientation or the shape of the tooth is correct comprises determining whether a ray defined by the selected point and the tangent vector intersects a surface of the tooth.

4. The method of claim 3, further comprising determining that the orientation of the tooth is not correct in response to determining that the ray intersects the surface of the tooth.

5. The method of claim 3, further comprising determining that the orientation or the shape of the tooth is correct in response to determining that the ray does not intersect the surface of the tooth.

6. The method of claim 1, further comprising:
modifying, by the computing device, the virtual dentition to create an updated shape or updated orientation for a tooth of the virtual dentition; and
determining, by the computing device, based on the tangent vector and the modified virtual dentition, whether the updated shape or a torque angle of the tooth is correct.

7. The method of claim 6, wherein modifying the virtual dentition comprises at least one of:
adjusting the torque angle of the tooth,
adjusting a shape of the tooth by adding or subtracting material from the tooth, or
adjusting a guidance tooth.

8. The method of claim 1, wherein performing the action comprises:
outputting, by the computing device, for display, a graphical user interface indicating at least a portion of the virtual dentition and the tangent vector.

9. The method of claim 1, wherein performing the action comprises:
determining, by the computing device, one or more treatment plans for the patient based at least in part on the tangent vector.

10. The method of claim 1, wherein determining the tangent vector comprises:
determining, by the computing device, the rotational axis of the virtual mandibular arch, wherein the selected point defines a radius of the circular arc; and
determining, by the computing device, the tangent vector as a tangent of the circular arc.

11. The method of claim 1, further comprising:
determining, by the computing device, a plurality of rotational axes, wherein each rotational axis of the plurality of rotational axes is associated with motion of the virtual mandibular arch in a respective direction of a plurality of directions;
determining, by the computing device, based on the plurality of rotational axes, a plurality of tangent vectors that are each indicative of a respective direction of motion of a plurality of directions of motion of the selected point; and
determining, by the computing device, based on at least one of the plurality of tangent vectors, whether a tooth of the virtual dentition will interfere with an antagonist tooth on an opposing arch.

12. The method of claim 11, wherein the selected point is associated with a wear facet on the tooth, and wherein performing the action comprises:
  identifying, by the computing device, from a plurality of directions of motion, at least one direction of motion that caused the wear facet.

13. The method of claim 12, wherein identifying the at least one direction of motion that is causing the wear facet further comprises:
  determining, by the computing device, a tangent vector of the plurality of tangent vectors that is parallel to a plane of the wear facet; and
  determining the at least one direction of motion based on the tangent vector that is parallel to the plane of the wear facet.

14. The method of claim 1, wherein the tangent vector indicates motion in at least one of: a lateral excursion, a protrusive excursion, a retrusive excursion, or an open or close excursion.

15. The method of claim 1, wherein performing the action comprises determining, by the computing device, whether a root orientation of a tooth of the virtual dentition is correct for axial loading on the tooth.

16. A non-transitory computer-readable storage medium storing instructions that, when executed, causes at least one processor of a computing system to perform the method of claim 1.

17. A computing system comprising:
  at least one processor; and
  memory comprising instructions that, when executed by the at least one processor, cause the at least one processor to:
    receive data indicative of a virtual dentition of an oral cavity of a patient, the data indicative of the virtual dentition including data indicative of at least one of a virtual mandibular arch representing a mandibular arch of the patient or a virtual maxillary arch representing a maxillary arch of the patient;
    receive data indicating a selected point on the virtual dentition of the oral cavity;
    determine, based on a rotational axis of the virtual mandibular arch, a tangent vector indicating a direction of motion of the selected point, wherein the rotational axis defines a center of a circular arc, the circular arc defining a plane that is perpendicular to the rotational axis; and
    perform an action to adjust the virtual dentition based on the tangent vector.

18. The computing system of claim 17, wherein execution of the instructions causes the at least one processor to perform the action by at least causing the at least one processor to determine, based on the tangent vector, whether an orientation of a tooth of the virtual dentition or a shape of the tooth is correct.

19. The computing system of claim 18, wherein execution of the instructions causes the at least one processor to determine whether the orientation or the shape of the tooth is correct by determining whether a ray defined by the selected point and the tangent vector intersects a surface of the tooth.

20. The computing system of claim 19, wherein execution of the instructions causes the at least one processor to determine whether the orientation of the tooth is not correct in response to determining that the ray intersects the surface of the tooth.

* * * * *